United States Patent [19]

Oxford

[11] Patent Number: 5,618,827

[45] Date of Patent: Apr. 8, 1997

[54] SUBSTITUTED PHENYLCARBAMATES AND PHENYLUREAS, THEIR PREPARATION AND THEIR USE AS 5-HT ANTAGONISTS

[75] Inventor: Alexander W. Oxford, Ware, Great Britain

[73] Assignee: Glaxo Group Limited, London, England

[21] Appl. No.: 307,567

[22] PCT Filed: Mar. 26, 1993

[86] PCT No.: PCT/EP93/00799

§ 371 Date: Sep. 21, 1994

§ 102(e) Date: Sep. 21, 1994

[87] PCT Pub. No.: WO93/20071

PCT Pub. Date: Oct. 14, 1993

[30] Foreign Application Priority Data

Mar. 31, 1992 [GB] United Kingdom ............. 9206989

[51] Int. Cl.[6] .................. A61K 31/445; C07D 413/10; C07D 417/10

[52] U.S. Cl. ............. 514/326; 546/187; 546/193; 546/209; 546/210

[58] Field of Search .................. 546/209, 210, 546/193, 187; 514/326

[56] References Cited

U.S. PATENT DOCUMENTS

| | | | |
|---|---|---|---|
| 5,132,309 | 1/1995 | Toth | 514/278 |
| 5,378,714 | 1/1995 | Hansen | 514/321 |

FOREIGN PATENT DOCUMENTS

| | | |
|---|---|---|
| 0007184 | 1/1980 | European Pat. Off. . |
| 0323077 | 7/1989 | European Pat. Off. . |
| 0419397 | 3/1991 | European Pat. Off. . |
| 0516520 | 12/1992 | European Pat. Off. . |
| 0526313 | 2/1993 | European Pat. Off. . |

OTHER PUBLICATIONS

Reeves et al., Br. J. Pharmacol., 103, 1991, pp. 1067–1072.
Archibald et al., Chemical Abstracts, 93, 11, 15 Sep. 1980, 106809f.
Nilsson et al., Chemical Abstracts, 70, 3, 20 Jan. 1969, 11519x.
Peroutka et al. "the neuropharmacology of serotonin" N.Y. Aca. Sci. 600:104–112 (section of Proutka), 195–196(section of Tyers) (1990).
Gotto, et al. "The role of receptors in biology and medicine" Raven Press, p. 191 (1987).
Clark et al. "Principles of psychopharmacology" Aca. Press, pp. 166–167 (1970).
Burger A. "Medicinal Chemistry" Intersci. Publisher, p. 496 (1960).
Burger A. "Medicineal Chemistry" Wiley Intersci. p. 66, (1971).
Nikolaeva et al. "Derivatives of cyclano[b]pyrrolidinic esters" CA 112:178525u (1990).
Ram et al. "Synthesis and biological activity of certain alkyl 5–alkoxycarbonyl– 1H–benzimidazole– 2–carbamates and related derivatives" J. Med. Chem. 35:539–547 (1992).
Jones et al. "The potential anxiolytic activity of GR38032F . . . " Br. J. Pharmacol. v. 93, 985–993 1988.

Primary Examiner—Ceila Chang
Attorney, Agent, or Firm—Bacon & Thomas

[57] ABSTRACT

Substituted phenylcarbamates and ureas of formula (I)

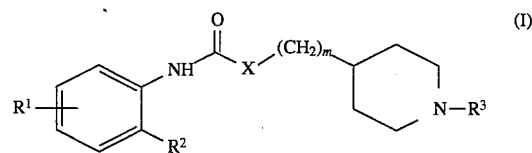

wherein $R^1$ represents a hydrogen or a halogen atom, or a $C_{1-6}$alkyl, $C_{1-6}$alkoxy or hydroxy group;

$R^2$ represents an oxadiazole or thiadiazole ring substituted by a group selected from $C_{1-6}$alkyl, $C_{3-7}$cycloalkyl, $-CH_2C_{2-5}$alkenyl, $-CH_2C_{2-5}$alkynyl, phenyl or benzyl;

X represents NH or an oxygen atom;

m represents zero, 1 or 2;

$R^3$ represents $C_{1-6}$alkyl, benzyl, $-(CH_2)_nR^4$ or

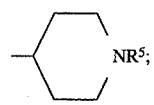

$R^4$ represents a group selected from cyano, hydroxyl, $C_{1-6}$alkoxy, phenoxy, $C(O)C_{1-6}$alkyl, $C(O)C_6H_5$, $-CONR^6R^7$, $-NR^6COR^7$, $-SO_2NR^6R^7$ or $-NR^6SO_2R^7$ (wherein each of $R^6$ and $R^7$ independently represent a hydrogen atom, a $C_{1-6}$alkyl or phenyl group);

n represents 2 or 3;

$R^5$ represents $COR^8$ or $SO_2R^8$ (wherein $R^8$ represents a hydrogen atom, a $C_{1-6}$alkyl or phenyl group);

and quaternary ammonium derivatives, piperidine N-oxides and pharmaceutically acceptable salts and solvates thereof; which compounds are potent and specific antagonists of 5-hydroxytryptamine (5HT; serotonin).

12 Claims, No Drawings

SUBSTITUTED PHENYLCARBAMATES AND PHENYLUREAS, THEIR PREPARATION AND THEIR USE AS 5-HT ANTAGONISTS

This invention relates to substituted phenylcarbamates and ureas, to processes for their preparation, to pharmaceutical compositions containing them and to their medical use.

European Patent Specification No. EP 0419397 describes compounds of formula

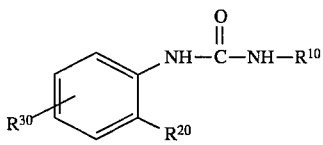

wherein
R$^{10}$ is a group

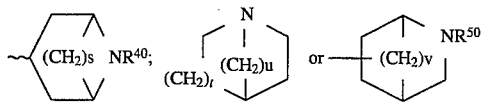

where S is 2 or 3, t is 1 or 2, u is 1 to 3, v is 1–3 and R$^{40}$ and R$^{50}$ are H, C$_{1-7}$alkyl or C$_{3-6}$cycloalkyl; and wherein R$^{20}$ is an oxadiazole, substituted with C$_{1-8}$alkyl, C$_{2-8}$alkenyl, C$_{2-8}$alkynyl, C$_{3-7}$cycloalkyl, benzyl, phenyl, C$_{1-6}$alkoxy, C$_{1-6}$alkylthio, amino or alkylamino; or wherein R$^{20}$ is —C—R$^{60}$=N—O—R$^{70}$, wherein R$^{60}$ is hydrogen or methyl and R$^{70}$ is C$_{1-6}$alkyl which may be substituted with C$_{3-7}$cycloalkyl;

and wherein R$^{30}$ is hydrogen, halogen, nitro, substituted amine, trifluoromethyl, C$_{1-6}$alkyl or C$_{1-6}$alkoxy.

These compounds are stated to have 5-HT$_3$-receptor antagonist activity, anti-emetic activity and/or gastric motility enhancing activity.

The present invention relates to novel compounds which are potent and specific antagonists of 5-hydroxytryptamine (5-HT serotonin).

Thus, the present invention provides substituted phenylcarbamates and ureas of formula (I):

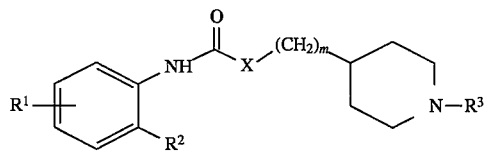

wherein R$^1$ represents a hydrogen or a halogen atom, or a C$_{1-6}$alkyl, C$_{1-6}$alkoxy or hydroxy group;

R$^2$ represents an oxadiazole or thiadiazole ring substituted by a group selected from C$_{1-6}$alkyl, C$_{3-7}$cycloalkyl, —CH$_2$C$_{2-5}$alkenyl, —CH$_2$C$_{2-5}$alkynyl, phenyl or benzyl;

X represents NH or an oxygen atom;

m represents zero, 1 or 2;

R$^3$ represents C$_{1-6}$alkyl, benzyl, —(CH$_2$)$_n$R$^4$ or

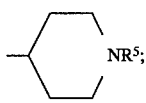

R$^4$ represents a group selected from cyano, hydroxyl, C$_{1-6}$alkoxy, phenoxy, C(O)C$_{1-6}$alkyl, C(O)C$_6$H$_5$, CONR$^6$R$^7$, —NR$^6$COR$^7$, —SO$_2$NR$^6$R$^7$ or —NR$^6$SO$_2$R$^7$ (wherein each of R$^6$ and R$^7$ independently represent a hydrogen atom, a C$_{1-6}$alkyl or phenyl group);

n represents 2 or 3;

R$^5$ represents COR$^8$ or SO$_2$R$^8$ (wherein R$^8$ represents a hydrogen atom, a C$_{1-6}$alkyl or phenyl group);

and quaternary ammonium derivatives, piperidine N-oxides and pharmaceutically acceptable salts and solvates thereof.

Suitable pharmaceutically acceptable salts of the compounds of general formula (I) include acid addition salts formed with pharmaceutically acceptable organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates.

Other acids, such as oxalic, while not in themselves pharmaceutically acceptable, may be useful in the preparation of salts useful as intermediates in obtaining the compounds of the invention and their pharmaceutically acceptable acid addition salts. The solvates may, for example, be hydrates.

References hereafter to a compound according to the invention includes both compounds of formula (I) and their quaternary ammonium derivatives, piperidine N-oxides and pharmaceutically acceptable acid addition salts together with pharmaceutically acceptable solvates.

Quaternary ammonium derivatives of compounds of formula (I) are compounds of formula

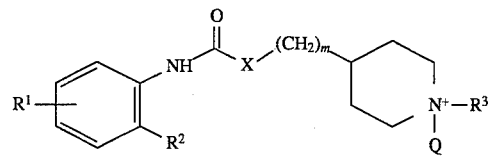

where Q represents C$_{1-6}$alkyl (e.g. methyl).

Piperidine N-oxides of compounds of formula (I) are compounds of formula

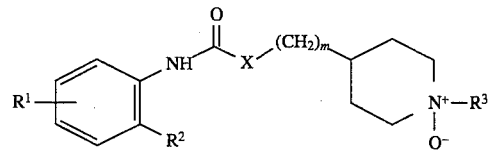

The oxadiazole or thiadiazole ring R$^2$ in the compounds of formula (I) may be a 1,2,4-oxadiazol-5-yl or -3-yl or 1,2,4-thiadiazol-5-yl or -3-yl, i.e.

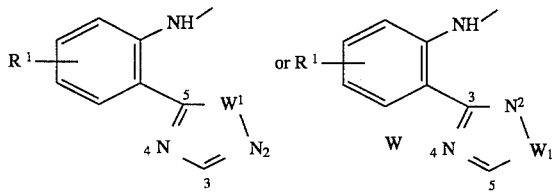

where W is —O— or —S—.

When the oxadiazole or thiadiazole ring is substituted, the substituent will be attached to the free carbon atom in the oxadiazole or thiadiazole ring.

All optical isomers of compounds of general formula (I) and their mixtures including the racemic mixtures thereof, and all the geometric isomers of compounds of formula (I), are embraced by the invention.

Referring to the general formula (I), a $C_{1-6}$alkyl group may be a straight chain or branched chain alkyl group, for example, methyl, ethyl, propyl, prop-2-yl, butyl, but-2-yl, 2-methylprop-2-yl, pentyl, pent-3-yl or hexyl. A —$CH_2C_{2-5}$alkenyl group may be, for example, a propenyl or butenyl group. A —$CH_2C_{2-5}$alkynyl group may be, for example, a prop-2-ynyl group. $C_{3-7}$cycloalkyl may be, for example, cyclopropyl, cyclobutyl or cyclohexyl.

When $R^1$ represents a halogen atom this may be, for example, a fluorine, chlorine, bromine or iodine atom. $R^1$ may be attached at any vacant position on the phenyl ring. For example, $R^1$ may be para to the —NH— substituent or para to $R^2$.

A preferred class of compounds of formula (I) is that in which $R^1$ represents a hydrogen atom, a halogen (e.g. fluorine) atom or a $C_{1-6}$alkyl (e.g. methyl) or $C_{1-6}$alkoxy (e.g. methoxy) group. Furthermore, when $R^1$ represents a halogen (e.g. fluorine) atom or a $C_{1-6}$alkyl (e.g. methyl) or $C_{1-6}$ alkoxy (e.g. methoxy) group this is preferably attached para to the —NH— substituent or para to $R^2$.

Another preferred class of compounds of formula (I) is that in which $R^2$ represents an oxadiazole or thiadiazole ring substituted by a $C_{1-6}$alkyl (e.g. methyl, prop-2-yl or butyl), $C_{3-7}$cycloalkyl (e.g. cyclopropyl), phenyl or benzyl group, for example a 1,2,4-oxadiazol-5-yl substituted in the 3-position by a $C_{1-6}$alkyl (e.g. methyl, prop-2-yl or butyl), $C_{3-7}$cycloalkyl (e.g. cyclopropyl), phenyl or benzyl group, or 1,2,4-oxadiazol-3-yl substituted in the 5-position by a $C_{1-6}$alkyl (e.g. methyl) group or a 1,2,4-thiadiazol-5-yl substituted in the 3-position by a $C_{1-6}$alkyl (e.g. methyl) group.

A preferred class of compounds of formula (I) is that in which $R^3$ represents $C_{1-6}$alkyl (e.g. prop-2-yl), benzyl,

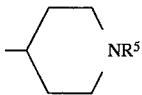

(where $R^5$ preferably represents $SO_2R^8$, e.g. $SO_2Me$) or, more preferably, —$(CH_2)_nR^4$.

When $R^3$ represents —$(CH_2)_nR^4$, a preferred class of compounds of formula (I) is that in which n represents 3 or, more preferably, 2 and $R^4$ represents a —$C_{1-6}$alkoxy (e.g. methoxy), —$CONR^6R^7$ (e.g. $CONH_2$), —$NR^6COR^7$ (e.g. NHCOMe), —$SO_2NR^6R^7$ (e.g. $SO_2NHMe$) or —$NR^6SO_2$—$R^7$ (e.g. $NHSO_2Me$ or $NMeSO_2Me$) group.

A further preferred class of compounds of formula (I) is that in which m represents 1.

Also preferred is the class of compounds of formula (I) where X represents an oxygen atom.

A preferred group of compounds of formula (I) is that in which $R^1$ represents a hydrogen or halogen (e.g. fluorine) atom, a $C_{1-6}$alkyl (e.g. methyl) or $C_{1-6}$alkoxy (e.g. methoxy) group (e.g. a hydrogen atom or a fluorine atom or methyl or methoxy group para to the —NH— substituent or para to $R^2$); $R^2$ represents an oxadiazole or thiadiazole ring substituted by a $C_{1-6}$alkyl (e.g. methyl, prop-2-yl or butyl), $C_{3-7}$cycloalkyl (e.g. cyclopropyl), phenyl or benzyl group, for example, a 1,2,4-oxadiazol-5-yl substituted in the 3-position by a $C_{1-6}$alkyl (e.g. methyl, prop-2-yl or butyl), $C_{3-7}$cycloalkyl (e.g. cyclopropyl), phenyl or benzyl group, a 1,2,4-oxadiazol-3-yl substituted in the 5-position by a $C_{1-6}$alkyl (e.g. methyl) group, or a 1,2,4-thiadiazol-5-yl substituted in the 3-position by a $C_{1-6}$alkyl (e.g. methyl) group; X represents NH or, more preferably, an oxygen atom; m represents zero, 2 or, more preferably, 1; $R^3$ represents $C_{1-6}$ alkyl (e.g. prop-2-yl), benzyl,

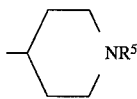

(where $R^5$ preferably represents $SO_2R^8$, e.g. $SO_2Me$) or, more preferably, —$(CH_2)_nR^4$ where n represents 3 or, more preferably, 2 and $R^4$ represents $C_{1-6}$alkoxy (e.g. methoxy), —$CONR^6R^7$ (e.g. $CONH_2$), —$NR^6COR^7$ (e.g. NHCOMe), —$SO_2NR^6R^7$ (e.g. $SO_2NHMe$) or —$NR^6SO_2R^7$ (e.g. $NHSO_2Me$ or $NMeSO_2Me$).

Specific compounds according to the invention are:
[1-[2-[(Methylsulphonyl)amino]ethyl]-4-piperidinyl]methyl [2-(3-methyl-1,2,4-oxadiazol-5-yl)phenyl]carbamate;

[1-[2-[(Methylsulphonyl)methylamino]ethyl]-4-piperidinyl] methyl[2-(3-methyl-1,2,4-oxadiazol-5-yl)phenyl]carbamate;

[1-[2-[(Methylsulphonyl)amino]ethyl]-4-piperidinyl]methyl [2-(3-methyl-1,2,4-thiadiazol-5-yl)phenyl]carbamate;

[1-[2-(Methylsulphonyl)amino]ethyl]-4-piperidinyl]methyl [4-methyl-2-(3-methyl-1,2,4-oxadiazol-5-yl)phenyl]carbamate;

[1-[2-[(Methylamino)sulphonyl]ethyl]-4-piperidinyl]methyl [2-(3-methyl-1,2,4-oxadiazol-5-yl)phenyl]carbamate;

[1-(2-Methoxyethyl)-4-piperidinyl]methyl[2-(3-methyl-1,2, 4-oxadiazol-5-yl)phenyl]carbamate;

[1-[3-[(Methylsulphonyl)amino]propyl]-4-piperidinyl]methyl[2-(3-methyl-1,2,4-oxadiazol-5-yl)phenyl]carbamate;

[1-[2-(Acetylamino)ethyl]-4-piperidinyl]methyl[2-(3-methyl-1,2,4-oxadiazol-5-yl)phenyl]carbamate di-p-toluoyl-1-tartrate;

N-[2-[4-[2-[[[[2-(3-Methyl-1,2,4-oxadiazol-5-yl)phenyl] amino]carbonyl]amino]ethyl]-1-piperidinyl]ethyl]methanesulphonamide;

1-[2-[(Methylsulphonyl)amino]ethyl]-4-piperidinyl[2-(3-methyl-1,2,4-oxadiazol-5-yl)phenyl]carbamate;

[1-(3-Amino-3-oxopropyl)-4-piperidinyl]methyl[2-(3-methyl-1,2,4-oxadiazol-5-yl)phenyl]carbamate;

[1'-(Methylsulphonyl)[1,4'-bipiperidin-4-yl]methyl[2-(3-methyl-1,2,4-oxadiazol-5-yl)phenyl]carbamate;

[1-[2-[(Methylsulphonyl)amino]ethyl]-4-piperidinyl]methyl [5-fluoro-2-(3-methyl-1,2,4-oxadiazol-5-yl)phenyl]carbamate;

N-[2-[4-[[[[[2-(3-Methyl-1,2,4-oxadiazol-5-yl)phenyl] amino]carbonyl]amino]methyl]-1-piperidinyl]ethyl] methanesulphonamide;

[1-[2-[(Methylsulphonyl)amino]ethyl]-4-piperidinyl]methyl [2-(3-cyclopropyl-1,2,4-oxadiazol-5-yl)phenyl]carbamate;

[1-[2-[(Methylsulphonyl)amino]ethyl]-4-piperidinyl]methyl [2-(3-phenyl-1,2,4-oxadiazol-5-yl)phenyl]carbamate;

[1-[2-[(Methylsulphonyl)amino]ethyl]-4-piperidinyl]methyl [2-[3-(1-methylethyl)-1,2,4-oxadiazol-5-yl]phenyl]carbamate;

[1-[2-[(Methylsulphonyl)amino]ethyl]-4-piperidinyl]methyl [2-[3-(phenylmethyl)-1,2,4-oxadiazol-5-yl]phenyl]carbamate;

1-[2-[(Methylsulphonyl)amino]ethyl]-4-piperidinyl]methyl [2-(3-methyl-1,2,4-oxadiazol-5-yl)phenyl]carbamate;

[1-[2-[(Methylsulphonyl)amino]ethyl]-4-piperidinyl]methyl][2-[3-(1,1-dimethylethyl)-1,2,4-oxadiazol-5-yl]phenyl]carbamate monohydrochloride;

[1-(1-Methylethyl)-4-piperidinyl]methyl[2-(methyl-1,2,4-oxadiazol-5-yl)phenyl]carbamate;

[1-(1-Methylethyl)-4-piperidinyl]methyl[2-(3-methyl-1,2,4-oxadiazol-5-yl)phenyl]carbamate;

N-[2-[4-[[[[2-(5-Methyl-1,2,4-oxadiazol-3-yl)phenyl] amino]carbonyl]amino]methyl]-1-piperidinyl]ethyl] methanesulphonamide;

[1-[2-[(Methylsulphonyl)methylamino]ethyl]-4-piperidinyl]methyl[2-(3-methyl-1,2,4-oxadiazol-5-yl)phenyl]carbamate;

N-(3-Methyl-1,2,4-oxadiazol-5-yl)-N'-[2-[1-(phenylmethyl)-4-piperidinyl]ethyl]urea;

1-(Phenylmethyl)-4-piperidinyl[2-(3-methyl-1,2,4-oxadiazol-5-yl)phenyl]carbamate;

[1-[(Phenylmethyl)-4-piperidinyl]methyl[2-(3-methyl-1,2,4-oxadiazol-5-yl)phenyl]carbamate;

and quarternary ammonium derivatives, piperidine N-oxides and pharmaceutically acceptable salts and solvates thereof.

The compounds of the invention are antagonists of 5-HT both in vitro and in vivo and are thus of use in the treatment of conditions mediated by 5-HT.

In particular the compounds of the invention inhibit the 5-HT induced contraction of guinea-pig colon (essentially following the general procedure described by C. J. Elswood et. al in Br. J. Pharmac., 1990, 100, (Proc. Suppl.) 485P and Eur. J. Pharmac., 1991, 196, 149–155 in the presence of ondansetron and methysergide) and the 5-HT-induced secretion in rat colon (as described by K T Bunce et. al in Br.J. Pharmac., 1991, 102, 811–816), and are thus useful in the treatment of 5-HT mediated disorders in which there is a disturbance of gastrointestinal function. Conditions involving disturbance of intestinal function include for example irritable bowel syndrome and-its associated pain, excessive gastrointestinal secretion, and/or diarrhoea for example diarrhoea associated with excessive gastrointestinal secretion, cholera infection and carcinoid syndrome. The compounds of the invention may also be useful in the treatment of emesis.

The compounds of the invention have been shown to be 5-$HT_4$ antagonists in vitro as demonstrated by their ability to inhibit the 5-HT-induced relaxation of the rat oesophagus preparation (essentially following the general procedure described by J J Reeves et al in Br. J Pharmac., 1989, 98. (Proc. Suppl.), 800P and 1991, 103, 1067–1072) and are thus of use in the treatment of conditions capable of amelioration by antagonism of such receptors. 5-$HT_4$ receptors have been found in, for example, the digestive and urinary tracts, brain and cardiovascular system of mammals, including man, and are thus believed to be associated with conditions involving the digestive and urinary tracts (e.g. urinary incontinence), cardiovascular system and CNS disorders.

Thus the compounds of the invention may also be useful in the treatment of movement disorders (e.g. Parkinsonism), psychoses such as schizophrenia, mania, dementia or other cognitive disorders e.g. Alzheimer's disease; depression; and dependency on drugs or substances of abuse.

The compounds of the invention have been shown to be active in the rat social interaction test as described by B J Jones et al in Br J Pharmac., 1988, 93, 985–93 and are thus of use in the treatment of anxiety.

In a further aspect the invention therefore provides a compound of formula (I) or a quaternary ammonium derivative, piperidine N-oxide or a pharmaceutically acceptable salt or solvate thereof for use in therapy, in particular in human medicine. It will be appreciated that use in therapy embraces but is not necessarily limited to use of a compound of the invention as an active therapeutic substance.

There is also provided as a further aspect of the invention the use of a compound of formula (I) or a quaternary ammonium derivative, piperidine N-oxide or a pharmaceutically acceptable salt or solvate thereof in the preparation of a medicament for use in the treatment of conditions mediated by 5-hydroxytryptamine, in particular conditions capable of amelioration by antagonism of 5-$HT_4$receptors.

In an alternative or further aspect there is provided a method for the treatment of a mammal, including man, comprising administration of an effective amount of a compound of formula (I) or a quaternary ammonium derivative, piperidine N-oxide or a pharmaceutically acceptable salt or solvate thereof in particular in the treatment of conditions mediated by 5-hydroxytryptamine, in particular conditions capable of amelioration by antagonism of 5-$HT_4$receptors.

It will be appreciated that reference to treatment is intended to include prophylaxis as well as the alleviation of established symptoms. Compounds according to the invention may be administered as the raw chemical but the active ingredient is preferably presented as a pharmaceutical formulation.

Accordingly, the invention also provides a pharmaceutical composition comprising a compound of formula (I) or a quaternary ammonium derivative, piperidine N-oxide or a pharmaceutically acceptable salt or solvate thereof and formulated for administration by any convenient route. Such compositions are preferably in a form adapted for use in medicine, in particular human medicine, and can conveniently be formulated in conventional manner using pharmaceutically acceptable carriers.

Thus the compounds according to the invention may be formulated for oral, buccal, parenteral, topical, implant or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

Preparations for oral administration may also be suitably formulated to give "pulsed release" i.e. rapid release of the active ingredient after an initial time delay. Such pulsed release formulations may further be enterically coated to allow targeting of drugs to the colon for either a direct local action, or to provide a preferred site for drug delivery.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal and pulmonary administration, the compounds according to the invention may be formulated as solutions or suspensions for administration via a suitable metered or unit dose device or alternatively as a powder mix with a suitable carrier for administration using a suitable delivery device.

For topical and percutaneous administration, the compounds according to the invention may be formulated as solutions, suspensions, creams or ointments and be included in systems that provide controlled release.

A proposed dose of the compounds of the invention for administration to man (of approximately 70 kg body weight) is 1 mg to 100 mg, of the active ingredient per unit dose expressed as the weight of free base, which could be administered, for example, 1 to 4 times per day. It will be appreciated that it may be necessary to make routine variations to the dosage, depending on the age and condition of the patient and the precise dosage will be ultimately at the discretion of the attendant physician or veterinarian. The dosage will also depend on the route of administration.

The compounds of the invention may, if desired, be administered in combination with one or more other therapeutic agents and formulated for administration by any convenient route in a conventional manner. Appropriate doses will be readily appreciated by those skilled in the art.

Compounds of formula (I), and quaternary ammonium derivatives, piperidine N-oxides and pharmaceutically acceptable salts or solvates thereof, may be prepared by the general methods outlined hereinafter. In the following description, the groups $R^1$ to $R^3$, X and m are as previously defined for compounds of formula (I) unless otherwise stated.

According to a first general process (A), a compound of formula (I) may be prepared by reacting a compound of formula (II) or (III):

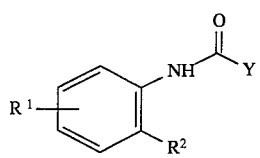                                     (II)

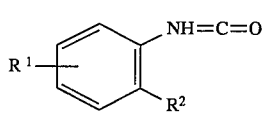                                     (III)

or a protected derivative thereof, wherein Y represents a leaving atom or group such as a halogen (e.g. chlorine) atom, with a compound of formula (IV):

                                     (IV)

where M is $NH_2$, OH or an activated derivative thereof (e.g. an alkali metal (e.g. lithium alkoxide), optionally in the presence of a strong acid such as methanesulphonic acid.

The reaction is conveniently effected in an inert organic solvent such as an ether (e.g. tetrahydrofuran) or a halogenated hydrocarbon (e.g. dichloromethane) at a temperature between −80° C. and the reflux temperature of the solvent. Alternatively, the reaction may take place by fusion in the absence of any solvent at an elevated temperature such as 100°–200° C., e.g. 140° to 175° C.

According to another general process (B), a compound of formula (I) may prepared by alkylating a compound of formula (V):

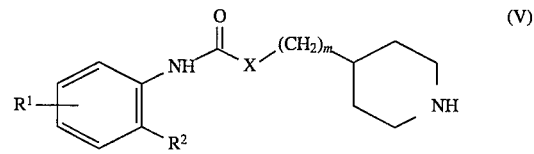                                     (V)

or a protected derivative thereof, with a compound of formula (VIa) or (VIb):

$LR^3$                                                    (VIa)

$CH_2=CH-R^{4a}$                                          (VIb)

wherein L represents a leaving atom or group such as a halogen (e.g. chlorine, bromine or iodine) atom, or an acyloxy (e.g. trifluoroacetyloxy) or a sulphonyloxy (e.g. p-toluenesulphonyloxy) group and $R^{4a}$ is an electron withdrawing group, i.e. $C(O)C_{1-6}$alkyl, $C(O)C_6H_5$, $CONR^6R^7$, $SO_2NR^6R^7$ (where $R^6$ and $R^7$ are as defined in formula (I)); or a protected derivative thereof, in the presence of a base such as a tertiary amine (e.g. diisopropylethylamine or triethylamine).

The reaction is conveniently effected in an inert organic solvent such as acetonitrile, a substituted amide (e.g. dimethylformamide) or an aromatic hydrocarbon (e.g. toluene), at an elevated temperature, for example at the reflux temperature of the solvent.

Alternatively compounds of formula (V) may be reacted with a compound of formula (VIc)

$O=R^3$                                                   (VIc)

in the presence of a reducing agent.

Suitable reducing agents include borohydrides such as sodium cyanoborohydride or sodium triacetoxyborohydride. Suitable solvents will depend upon the reducing agent used, but may include alcohols, for example, methanol or ethanol, halogenated hydrocarbons, for example, 1,2-dichloroethane or ethers, for example, diethyl ether or tetrahydrofuran. The reaction conveniently takes place at ambient temperature.

According to another general process (C), a compound of formula (I) where $R^2$ is a 1,2,4-oxadiazol-3-yl group may be prepared by reacting a compound of formula (VII)

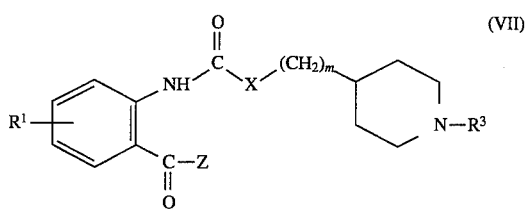

where Z is $C_{1-6}$alkoxy (e.g. methoxy), with a compound of formula (VIII)

where $R^9$ is a substituent as defined for $R^2$, in the presence of a strong base such as sodium hydride.

The reaction conveniently takes place in a suitable solvent such as an ether (e.g. tetrahydrofuran) at an elevated temperature, such as the reflux temperature of the reaction mixture.

According to another general process (D), a compound of formula (I) where $R^2$ is a 1,2,4-thiadiazol-5-yl group may be prepared by reacting a compound of formula (IX)

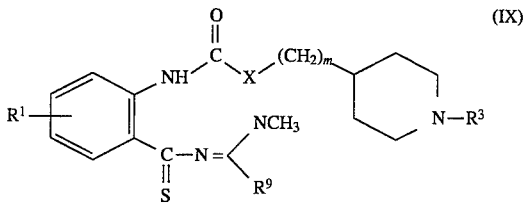

where $R^9$ is as defined above, with hydroxylamine-O-sulfonic acid, optionally in the presence of a base such as pyridine.

The reaction conveniently takes place in a suitable solvent such as an alcohol (e.g. methanol) at ambient temperature.

According to a further general process (E), a compound of formula (I), where $R^2$ is a represents a group $-(CH_2)_nR^4$ where $R^4$ is a group $NH-SO_2R^7$, may be prepared by reacting a compound of formula (X)

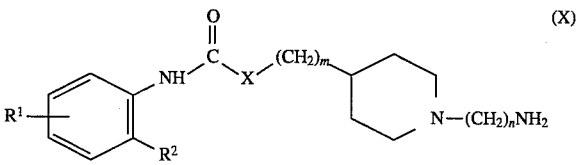

with a compound (XI)

where hal is a halogen (e.g. chlorine) atom, in the presence of a base (e.g. pyridine).

The reaction conveniently takes place in a suitable solvent such as a halogenated hydrocarbon (e.g. dichloromethane) at ambient temperature.

According to another general process (F), a compound of formula (I) may be converted into another compound of formula (I) using conventional techniques.

Thus, for example, compounds of formula (I) where $R^3$ represents a group containing an $-NH-$ moiety may be converted into another compound of formula (I) wherein $R^3$ contains a $-N(C_{1-6}alkyl)-$ moiety (e.g. $-N(CH_3)-$) using a suitable alkylating agent such as an alkyliodide e.g. methyliodide) as described above. The reaction conveniently takes place in a suitable solvent such as an ether (e.g. tetrahydrofuran) at ambient temperature and in the presence of a strong base such as sodium hydride.

Also, quaternary ammonium salts of compounds of formula (I) may be prepared by reacting non-quaternary compounds of formula (I) with a suitable quaternising agent such as Q—L (where L is a leaving group as defined above e.g. a halogen (e.g. iodine) atom and Q is as defined above). The reaction conveniently takes place in a suitable solvent such as a chlorinated hydrocarbon (e.g. chloroform) at ambient temperature.

Piperidine N-oxides of compounds of formula (I) may be prepared by reacting an appropriate piperidine compound of formula (I) with a suitable oxidising agent such as 3-chloro peroxybenzoic acid. Oxidation conveniently takes place in a suitable solvent such as a halogenated hydrocarbon (e.g. chloroform) at ambient temperature.

It should be appreciated that in the above transformations it may be necessary or desirable to protect any sensitive groups in the molecule of the compound in question to avoid undesirable side reactions. For example when R) represents a hydroxyl group it may be necessary to protect the hydroxyl group, for example with an arylmethyl (e.g. benzyl or trityl) group. It may also be necessary to protect compounds where $R^3$ contains other sensitive groups such as an amine group. Such groups may be protected for example using an acyl group (e.g. benzyloxycarbonyl) or a silyl group (e.g. trimethylsilyl).

Thus according to another general process (G), a compound of general formula (I) may be prepared by the removal of any protecting groups from a protected form of a compound of formula (I). Deprotection may be effected using conventional techniques such as those described in 'Protective Groups in Organic Synthesis 2nd Ed.' by T. W. Greene and P G M Wuts (John Wiley and Sons, 1991).

Compounds of formula (II) where Y is chlorine may be prepared, for example, by reacting a compound of formula (XII):

with phosgene.

Compounds of formula (III) are either known or may be prepared from known compounds by conventional procedures. For example, the compounds may be prepared by treatement of the corresponding aniline of formula (XII) with phosgene followed by a strong base such as triethylamine.

Compounds of formula (V) may be prepared, for example, by reacting a compound of formula (XIII)

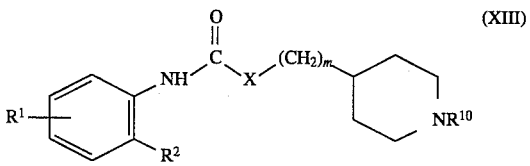

wherein $R^{10}$ is a $C_{1-6}$alkyl (e.g. methyl) group with a chloroformate (e.g. 1-chloroethyl chloroformate, vinylchloroformate or ethylchloroformate) at an elevated temperature, with subsequent heating of the reaction mixture at reflux temperature with an alcohol (e.g. methanol).

Compounds of formula (XII) may be prepared according to the method of general process (A), by reacting a compound of formula (II) with a compound of formula (XIV)

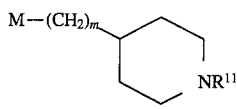

(XIV)

where M is as defined above and $R^{11}$ is a $C_{1-6}$alkyl (e.g. methyl) group.

Compounds of formula (VII) may be prepared by reacting compounds of formula (XV) or (XVI)

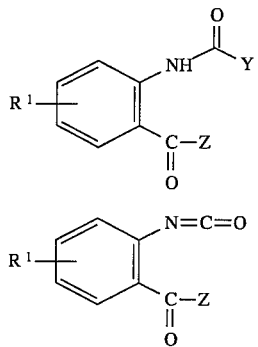

where Y and Z are as defined above, with a compound of formula (IV) as defined above, under conditions as described above for process (A).

Compounds of formula (IX) may be prepared by reacting a compound of formula (XVII)

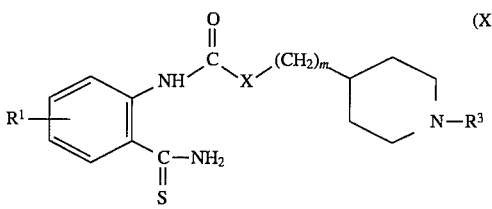

with a compound of formula (XVIII)

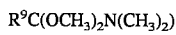

$R^9C(OCH_3)_2N(CH_3)_2)$ (XVIII)

where $R^9$ is as defined above.

The reaction conveniently takes place in a suitable solvent such as an amide (e.g. dimethylformamide) at ambient temeprature.

Compounds of formula (XVII) may be prepared by reacting compounds of formulae (XIX) or (XX)

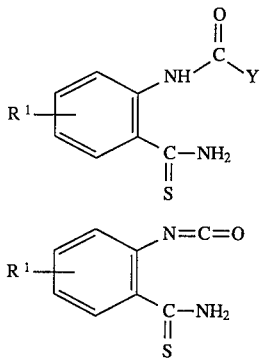

or a protected derivative thereof, where Y is as defined above, with a compound of formula (IV) as defined above, under conditions as described above for process (A), followed by removal of any protecting groups present.

Compounds of formula (X) may be prepared by reacting a compound of formula (V) with an appropriate alkylating agent under conditions as described in process (B).

Compounds of formulae (V), (VII), (IX), (X), (XIII) and (XVIII) are novel and therefore form a further feature of the invention. The remaining compounds are either known, or may be prepared from known compounds by conventional procedures.

In addition, compounds of formula (IV) may be prepared by reduction of the corresponding compounds of formula (XXI)

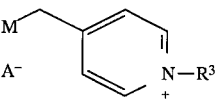

(XXI)

wherein $A^-$ represents an associated anion such as a halide (e.g. bromide) anion and M is as defined above. Reduction may be conveniently effected by hydrogenation in the presence of a suitable catalyst, such as rhodium on alumina, in the presence of a suitable solvent, for example under aqueous conditions.

Compounds of formula (XXI) may be prepared by alkylation of 4-pyridine methanol or 4-pyridine methylamine (in which the amino group has been protected with a suitable protecting group) using a suitable alkylating agent of formula (VIa) as defined hereinbefore. The reaction conveniently takes place in the presence of sodium iodide in a suitable solvent such as an alcohol (e.g. isopropanol) at the reflux temperature of the solvent.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

The compounds of the invention may readily be isolated in association with solvent molecules by crystallisation from or evaporation of an appropriate solvent to give the corresponding solvates.

Individual enantiomers of the compounds of the invention may be obtained by resolution of a mixture of enantiomers (e.g. a racemic mixture) using conventional means, such as an optically active resolving acid; see for example Stereochemistry of Carbon Compounds' by E. L. Eliel (McGraw Hill, 1962) and 'Tables of Resolving Agents' by S. H. Wilen.

The various general methods described above may be used for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in °C. Thin layer chromatography (t.l.c.) was carried out on silica, and flash column chromatography (FCC) on silica (Merck 9385). Solvent System A as used for chromatography denotes dichloromethane:ethanol:0.88 ammonia solution. Organic extracts were dried, where indicated, over magnesium sulphate.

INTERMEDIATE 1

[2-(3-Methyl-1,2,4-oxadiazol-5-yl)phenyl]carbamoyl Chloride

A solution of 2-(3-methyl-1,2,4-oxadiazol-5-yl)benzenamine (1.0 g) in dry dichloromethane (20 ml) was added dropwise to a 0° solution of phosgene (14.1 ml, 20% in toluene) in dry dichloromethane (50 ml) under a nitrogen atmosphere. After addition the reaction mixture was allowed to slowly attain room temperature and stirred for 4 h. Nitrogen, was bubbled through the resulting mixture for 16 h. Dichloromethane was added to the resultant precipitate and the solution was evaporated to give the title compound (1.322 g), $\nu_{max}$ (Nujol) 2800–2500, 1782 (NCO-Cl), 1631 (C=N), 1501 (NH), 769 (aromatic) cm$^{-1}$.

INTERMEDIATE 2

N-[2-[4-(Hydroxymethyl)-1-piperidinyl]ethyl]methanesulphonamide

4-Piperidine methanol (1.60 g) was dissolved in dry acetonitrile (40 ml), N,N-diisopropylethylamine (5 ml) was added, followed by N-(2-bromoethyl)methanesulphonamide (2.95 g) in acetonitrile (10 ml), and the resulting mixture heated at reflux for 2 h. The solvent was removed in vacuo to leave a gum. This was purified by FCC eluting with System A (75:8:1) to give the title compound (1.80 g) as a solid, m.p. 81°–82°.

INTERMEDIATE 3

Methyl 2-[(chlorocarbonyl)amino]benzoate

A solution of methyl anthranilate (6.0 g) in dichloromethane (50 ml) was added dropwise over 15 min to a 0° solution of phosgene (20% in toluene, 100 ml) in dichloromethane (50 ml) under a nitrogen atmosphere. After addition the resulting opaque solution was stirred at room temperature for 5 h before concentrating to dryness to give the title compound as a white solid (8.0 g), m.p. 80°–82°.

Similarly prepared:

INTERMEDIATE 4

[4-Methoxy-2-(3-methyl-1,2,4-oxadiazol-5-yl)phenyl]carbamoyl Chloride (2 g), mp>320° (dec).

From [4-methoxy-2-(3-methyl-1,2,4-oxadiazol-5-yl)]benzenamine (1.5 g)

INTERMEDIATE 5

Methyl 2-[[[[1-[2-[(methylsulphonyl)amino]ethyl]-4-piperidinyl]methoxy]carbonyl]amino]benzoate A well mixed powder phase of methyl 2-[(chlorocarbonyl)amino]benzoate and N-[2-[4-(Hydroxymethyl)-1-piperidinyl]ethyl]methanesulphonamide (2.43 g) under a nitrogen atmosphere was lowered into a pre-heated oil bat at 150°. After 35 min the mixture was cooled and dissolved in dichloromethane (50 ml) and 8% sodium bicarbonate solution (50 ml). The aqueous was separated and further extracted dichloromethane (2×30 ml). Combined organics were washed with saturated brine (30 ml), dried and concentrated to give a viscous oil (3.3 g). FCC using System A (95:5:0.5) as eluant afforded the title compound as a white solid (1.82 g) m.p. 106°–108°.

INTERMEDIATE 6

4-Methoxy-2-(3-methyl-1,2,4-oxadiazol-5-yl)benzenamine

Sodium hydride (594 mg) was added to a stirred suspension of acetamide oxime (1.0 g) and 4 molecular sieves (4 g) in dry tetrahydrofuran (50 ml) under nitrogen. The mixture was heated at 60° for 30 min then allowed to cool to room temperature. A solution of 2-amino-5-methoxybenzoic acid, methyl ester (2.0 g) in dry tetrahydrofuran (20 ml) was added and the mixture stirred at reflux for 2.5 h. The suspension was allowed to cool, filtered and the filtrate evaporated to give the title compound as a yellow solid (1.64 g)

T.l.c. (cyclohexane:ethyl acetate 9:1) Rf=0.20

Similarly prepared:

INTERMEDIATE 7

4-Methyl-2-(3-methyl-1,2,4-oxadiazol-5-yl)benzenamine (1.19 g), m.p. 92.5°–95.5°

From acetamide oxime (821 mg) and 2-amino-5-methylbenzoic acid, methylester (1.5 g) with further purification by FCC using 10% ethyl acetate in cyclohexane as eluant.

INTERMEDIATE 8

5-Fluoro-2-(3-methyl-1,2,4-oxadiazol-5-yl)benzenamine

From acetamide oxime (3.52 g) and 2-amino-4-fluorobenzoic add, ethyl ester (6.96 g), to give a brown-green solid (ca. 6 g) which was further purified by FCC using 20% diethyl ether in cyclohexane as eluant to give an off-white solid (3.4 g). Triturition of a 900 mg portion in cyclohexane (9 ml) gave the title compound (520 mg).

Repeating the trituration on all crude material gave further title compound as a white powder (2.184 g) m.p. 146.5°–148.2°.

INTERMEDIATE 9

4-Piperidinylmethyl[2-(3-methyl-1,2,4-oxadiazol-5-yl)phenyl]carbamate Hydrochloride

[1-[(Phenylmethyl)-4-piperidinyl]methyl[2-(3-methyl-1,2,4-oxadiazol-5-yl)phenyl]carbamate (300 mg) and 1-chloroethyl chloroformate (1.32 ml) were heated together at 50° for 2 h. Methanol (1.8 ml) was added and the mixture heated at reflux for 0.5 h. The solvent was removed in vacuo to give a yellow solid (300 mg) which was purified by FCC with eluant System A (90:10:1). Further elution with System A (25:10:1) afforded the free base of the title compound as a solid (217 mg).

T.l.c. (System A 25:10:1) Rf 0.46.

The free base was dissolved in methanol (10 ml) and maleic acid (71 mg) in methanol was added. The solvent was removed in vacuo and the residual oil was triturated with ether to yield a brown solid (237 mg). The solid was converted to the free base using column chromatography with System A (70:30:3) as eluant to yield the free base (155 mg) as a clear oil.

T.l.c (System A, 70:30:3) Rf 0.29. The free base was dissolved in dichloromethane and ethereal hydrogen chloride was added. Concentration to dryness followed by trituration with ether gave the title compound as a cream solid (136 mg).

Analysis Found C,52.3; H,5.8; N,15.1;
$C_{16}H_{20}N_4O_3 \cdot HCl \cdot H_2O$ requires: C,51.8; H,6.2; N,15.1%
Water analysis shows 1.61% $H_2O$ w/w

INTERMEDIATE 10

4-Piperidinyl [2-(3-methyl-1,2,4-oxadiazol-5-yl)phenyl]carbamate

A solution of 1-(phenylmethyl)-4-piperidinyl[2-(3-methyl-1,2,4-oxadiazol-5-yl)phenyl]carbamate (1.0 g) in 1-chloroethyl chloroformate (5.5 ml) was stirred at 50° under nitrogen for 3 h. Methanol (6.2 ml) was added and the mixture stirred at reflux for a further 2 h. The solvent was removed in vacuo to give an off-white solid (~900 mg). FCC with System A (100:10:1) as the eluent gave the title compound as a white solid (500 mg) m.p. 141°–2°.

Similarly prepared:

INTERMEDIATE 11

N-[2-(3-methyl-1,2,4-oxadiazol-5-yl)phenyl]-N'-[2-(4-piperidinyl)ethyl]urea (450 mg)

T.l.c. (System A, 25:10:1), Rf=0.25

From N-(3-Methyl-1,2,4-oxadiazol-5-yl)-N'-[2-[1-(phenylmethyl)-4-piperidinyl]ethyl]urea (1.25 g). A sample of the free-base above (150 mg) was dissolved in dry dichloromethane (2 ml) and treated with an excess of ethereal hydrogen chloride solution. The solvent was removed in vacuo and the residue triturated with dry ether (5×5 ml) to give the hydrochloride salt of the title compound as a light brown solid (160 mg), m.p. 129°–132°.

INTERMEDIATE 12

N-2-[[[1-(Dimethylamino)ethylidene]amino]thioxomethyl]phenylacetamide

N-[2-(Aminothiooxomethyl)phenyl]-acetamide (3.500 g) was dissolved in dimethylformamide (60 ml). Dimethyl acetamide dimethyl acetal (6.5 ml) was added and the dark red solution stirred under a nitrogen atmosphere at room temperature for 5 h. Concentration in vacuo gave the title compound as a red oil, (5.1 g).

T.l.c (System A 300:8:1) Rf0.35

INTERMEDIATE 13

N-[2-(3-Methyl-1,2,4-thiadiazol-5-yl)phenyl]acetamide

N-[2-[[[1-(Dimethylamino)ethylidene]amino]thioxomethyl]phenyl]acetamide (5.1 g) and hydroxylamine-o-sulfonic acid (3.048 g) were dissolved in methanol (60 ml). Pyridine (2.9 ml) was added and the resulting solution was stirred under nitrogen at room temperature for 24 h. Concentration in vacuo gave a brown solid. This was separated between sodium carbonate solution (60 ml) and dichloromethane (50 ml), the aqueous extracted with fresh dichloromethane (5×30 ml) and the combined organic extracts dried. Concentration in vacuo gave a brown solid (3.3 g) which was dissolved in ethanol (20 ml), and purified by FCC using cyclohexane:ethyl acetate (60:40) as eluant to give the title compound as a yellow-brown solid (2.98 g). T.l.c. (cyclohexane:ethyl acetate, 60:40) RF 0.55.

INTERMEDIATE 14

2-(3-Methyl-1,2,4-thiadiazol-5-yl)benzenamine

N-[2-(3-Methyl-1,2,4-thiadiazol-5-yl)phenyl]acetamide (1.487 g) was dissolved in Claisen's alkali (6.3M KOH in methanol, 12 ml) and refluxed under a nitrogen atmosphere for 16 h, then cooled and extracted with ethyl acetate (3×40 ml). The combined organic extracts were washed with sodium chloride solution (10 ml), dried and concentrated in vacuo to give an orange powder (1.1 g). FCC using cyclohexane:ethyl acetate (4:1) as eluant gave the title compound as a yellow solid, (302 mg). T.l.c (cyclohexane:ethyl:acetate, 4:1) Rf 0.6

INTERMEDIATE 15

[2-(5-Methyl-1,2,4-oxadiazol-3-yl)phenyl]carbamoyl Chloride

A solution of 2-(5-methyl-1,2,4-oxadiazol-3-yl)benzenamine (1.0 g) in dry dichloromethane (20 ml) was added dropwise to a solution of phosgene (14.1 ml) in dichloromethane (50 ml) at 0° under a nitrogen atmosphere. The opaque solution was then allowed to slowly attain room temperature and stirred for 17 h. The reaction mixture was concentrated under vacuo to give a pale yellow solid (1.3 g).

m.p. 165° dec.

INTERMEDIATE 16

[1-(2-Aminoethyl)-4-piperidinyl]methyl[2-(3-methyl-1,2,4-oxadiazol-5-yl)phenyl]carbamate A solution of 4-piperidinylmethyl[2-(3-methyl-1,2,4-oxadiazol-5-yl)phenyl]carbamate (200 mg), 2-bromoethylamine hydrobromide (130 mg) and diisopropylethylamine (0.33 ml) in dry acetonitrile (10 ml) was stirred at reflux under nitrogen for 6 h. The solvent was removed in vacuo to give a semi-solid (~675 mg). FCC using System A (75:10:1) as the eluent gave the title compound as a colourless oil (158 mg).

T.l.c. (System A 75:10:1) Rf 0.35.

EXAMPLE 1

1-[2-[(Methylsulphonyl)amino]ethyl]-4-piperidinyl]methyl[2-(3-methyl-1,2,4-oxadiazol-5-yl)phenyl]carbamate A solution of phosgene in toluene (12.5% w/v: 100 ml) was added to 2-(3-methyl-1,2,4-oxadiazol-5-yl)benzenamine (2.5 g) and the heterogeneous mixture was stirred at reflux under nitrogen for 2 h. Additional toluene (70 ml) was added and the mixture was stirred at reflux for a further 30 min. After cooling, the reaction was evaporated to dryness and the resulting solid was treated with N-2-[4-(hydroxymethyl)-1-piperidinyl]ethyl]methanesulphonamide (3.1 g) and 1,2-dichlorobenzene (mol. sieve-dried, 100 ml) and stirred at 120° under nitrogen for 18½ h. The mixture was cooled to ca. 10° and diluted with cyclohexane (100 ml). The solid was collected by filtration, mixed with 8% sodium bicarbonate solution and extracted with 10% ethanol in dichloromethane (1×100 ml then 6×50 ml). The combined organic extract was dried ($Na_2SO_4$) and evaporated to dryness and the residue purified by FCC eluting with System A (100:8:1) to give a beige solid which material was recrys tallised from cyclohexane:ethyl acetate (ca. 140 ml:40 ml) to give the title compound (1.65 g)

as white microneedles, m.p. 129°–130°

Analysis Found: C,52.4; H,6.4; N,15.2;

$C_{19}H_{27}N_5O_5S.0.18C_4H_8O_2$ requires C,52.2; H,6.3; N,15.45%

EXAMPLE 2

[1-[2-[Methylsulphonyl)amino]ethyl]-4-piperidinyl]methyl[2-(3-methyl-1,2,4-oxadiazol-5-yl)phenyl]carbamate (Z)-2-butenedioate Salt (1:1)

[1-[2-[(Methylsulphonyl)amino]ethyl]-4-piperidinyl]methyl[2-(3-methyl-1,2,4-oxadiazol-5-yl)phenyl]carbamate (1.541 g) was dissolved in warm methanol (30 ml) and treated with a methanolic solution (5 ml) of maleic acid (0.409 g). The resulting solution was evaporated to dryness. The cream solid was triturated with warm ethyl acetate and dried in vacuo to give the title compound (1.36 g), m.p. 163°–164°.

Analysis Found: C,49.7; H,5.6; N,12.45;

$C_{19}H_{27}N_5O_5.C_4H_4O_4$ requires C,49.9; H,5.6; N,12.65%

EXAMPLE 3

[1-[2-[(Methylsulphonyl)amino]ethyl]-4-piperidinyl]methyl[2-(3-methyl-1,2,4-oxadiazol-5-yl)phenyl]carbamate

[2-(3-Methyl-1,2,4-oxadiazol-5-yl)phenyl]carbamoyl chloride (7.5 g) was placed in a flask equipped with an air stirrer and ground to a powder N-[2-[4-(Hydroxymethyl)-1-piperidinyl]ethyl]methanesulphonamide (9.33 g) was added and the solids intimately mixed under nitrogen for 10 min at room temperature. The mixture was stirred under a stream of nitrogen at 150° for 10 min. The mixture was allowed to cool then toluene/ethanol (10:1; 110 ml) was cautiously added followed by 8% sodium bicarbonate solution. The mixture was vigorously stirred, the layers were separated and the aqueous phase extracted with 10% ethanol in dichloromethane (4×100 ml). The organic solutions were combined and dried and concentrated in vacuo to give a beige solid. This was purified by FCC eluting with System A (100:8:1) to give the title compound (11.83 g) as fluffy off-white needles.

T.l.c. (System A 100:8:1) Rf 0.44

EXAMPLE 4

[1-[2-[(Methylsulphonyl)amino]ethyl]-4-piperidinyl]methyl[2-(3-methyl-1,2,4-oxadiazol-5-yl)phenyl]carbamate (Z)-2-butenedioate Salt (1:1)

[1-[2-[(Methylsulphonyl)amino]ethyl]-4-piperidinyl]methyl[2-(3-methyl-1,2,4-oxadiazol-5-yl)phenyl]carbamate (11.83 g) was dissolved in warm methanol/dichloromethane (50 ml/25 ml) and treated with a warm solution of maleic acid (2.91 g) in methanol (25 ml). The resultant solution was concentrated in vacuo to give a viscous gum which rapidly solidified upon standing. The beige solid was crystallised from absolute ethanol (500 ml) to give the title compound (12.25 g) as fluffy white microneedles, m.p. 163°–164°.

Analysis Found: C,50.15; H,5.7; N,12.6;

$C_{19}H_{27}N_5O_5S.C_4H_4O_4$ requires C,49.9; H,5.6; N,12.65; S,5.8%

H.p.l.c. found the material to be 99% pure.

EXAMPLE 5

[1-[2-[(Methylsulphonyl)methylamino]ethyl]4-piperidinyl]methyl[2-(3-methyl-1,2,4-oxadiazol-5-yl)phenyl]carbamate To a stirred solution of [1-[2-[(methylsulphonyl)amino]ethyl]-4-piperidinyl]methyl[2-(3-methyl-1,2,4-oxadiazol-5-yl)phenyl]carbamate (190 mg) in dry, THF (5 ml) was added tetrabutyl ammonium fluoride (1.10 ml, 1.0M solution in THF). After 30 min methyl iodide (0.03 ml) was added and the suspension stirred for 2.5 h. The mixture was poured into 8% sodium bicarbonate (25 ml) solution, extracted with dichloromethane (4×10 ml), and the combined organic layers were dried and evaporated to give a yellow solid (414 mg). The solid was purified by column chromatography using System A (300:8:1) as eluant to give a white solid (224 mg). FCC using System A (400:8:1) as eluant gave the title compound (55 mg) as a white solid.

T.l.c. (System A 300:8:1) Rf 0.35

EXAMPLE 6

[1-[2-[(Methylsulphonyl)methylamino]ethyl]4-piperidinyl]methyl[2-(3-methyl-1,2,4-oxadiazol-5-yl)phenyl]carbamate (Z)-2-butenedioate Salt (1:1)

[1-[2-[(Methylsulphonyl)methylamino]ethyl]-4-piperidinyl]methyl[2-(3-methyl-1,2,4-oxadiazol-5-yl)phenyl]carbamate (55 mg) was dissolved in boiling ethyl acetate (1 ml) and maleic acid (17 mg) in hot ethyl acetate (1 ml) added. White crystals precipitated. These were filtered and dried under vacuum to give the title compound (51 mg), as a white powder, m.p. 170°–172°

Analysis Found: C,50.77; H,5.91; N,12.21;

$C_{20}H_{29}N_5O_5S.C_4H_4O_4$ requires: C,50.78; H,5.86; N,12.34%

EXAMPLE 7

[1-[2-[(Methylsulphonyl)amino]ethyl]-4-piperidinyl]methyl[2-(3-methyl-1,2,4-thiadiazol-5-yl)phenyl]carbamate A solution of 2-(3-methyl-1,2,4-thiadiazol-5-yl)benzenamine (302 mg) in dry acetonitrile (20 ml) was cautiously added to a 0° solution of phosgene (20% in toluene, 5 ml). The resulting suspension was stirred overnight at room temperature under nitrogen. The solution was concentrated in vacuo to give a white solid (0.37 g), which was ground to powder using an air stirrer. N-[2-[4-(hydroxymethyl-1-piperidinyl]ethyl]methanesulphonamide, (450 mg) was added. The two solids were stirred for 10 min and then lowered into an oil bath at 175° where they were stirred under nitrogen for 25 min. The resultant oil was cooled and separated between sodium bicarbonate (30 ml) and 10% ethanol in toluene (30 ml). The aqueous suspension was extracted with 10% ethanol in dichloromethane (3×20 ml).

The combined organic extracts were dried and concentrated in vacuo to give a brown oil (0.7 g), which crystallised on standing. FCC using System A (200:8:1) as eluant gave, on concentration of the appropriate fractions, the title compound (345 mg).

T.l.c. (System A, 200:8:1) Rf 0.3

Similarly Prepared:

EXAMPLE 8

[1-[2-(Methylsulphonyl)amino]ethyl]-4-piperidinyl]
methyl[4-methyl-2-(3-methyl-1,2,4-oxadiazol-5-
yl)phenyl]carbamate (74 mg)

T.l.c. (System A, 200:8:1) Rf 0.25

From 4-methyl-2-(3-methyl-1,2,4-oxadiazol-5-yl)benzenamine (600 mg) and N-[2-[4-(hydroxymethyl)-1-piperidinyl]ethyl]methanesulphonamide (790 mg).

EXAMPLE 9

[1-[2-[Methylsulphonyl)amino]ethyl]-4-piperidinyl]
methyl[2-(3-methyl-1,2,4-thiadiazol-5-yl)phenyl]
carbamate, Maleate

[1-[2-[(Methylsulphonyl)amino]ethyl]-4-piperidinyl]methyl[2-(3-methyl-1,2,4-thiadiazol-5-yl)phenyl]carbamate (345 mg) was dissolved in dichloromethane (10 ml). A solution of maleic acid (95 mg) in warm ethyl acetate (10 ml) was added. The resultant precipitate was collected by filtration and dried to give the title compound, (397 mg) m.p. 139°–140°.

Analysis: Found: C,48.53; H,5.69; N,11.89; S,11.26;

$C_{19}H_{27}N_5O_4S_2.C_4H_4O_4$ requires: C,48.49; H,5.49; N,12.29; S,11.26%

EXAMPLE 10

[1-[2-(Methylsulphonyl)amino]ethyl]-4-piperidinyl]
methyl[4-methyl-2-(3-methyl-1,2,4-oxadiazol-5-
yl)phenyl]carbamate Fumerate (1:1)

[1-[2-(Methylsulphonyl)amino]ethyl]-4-piperidinyl]methyl[4-methyl-2-(3-methyl-1,2,4-oxadiazol-5-yl)phenyl]carbamate (74 mg) was dissolved in boiling ethyl acetate (4 ml). A solution of maleic acid (22 mg) in warm ethyl acetate (1.5 ml) was added. The resultant precipitate was collected by filtration and dried in vacuo to give a solid (61 mg). N.m.r. showed an aromatic impurity. For this reason the solid was cleaved with 2N sodium hydroxide (10 ml). The free base was extracted with dichloromethane (3×10 ml). The organic layers were dried and concentrated in vacuo to give a white powder, (54 mg). The free base was dissolved in boiling ethyl acetate (3 ml). A solution of fumaric acid (26 mg) in warm ethyl acetate (5 ml) was added. The resulting precipitate was collected by filtration and dried in vacuo to give the title compound (37 mg), m.p. 174°–175°.

N.m.r. shows ca. 1.8 molar equivalents fumaric acid

Analysis Found: C,49.47; H,5.61; N,10.80;

$C_{20}H_{29}N_5O_5S.1.8C_4H_4O_4$ requires: C,49.46; H,5.52; N,10.60%

EXAMPLE 11

[1-[2-[(Methylsulphonyl)amino]ethyl]-4-piperidinyl]
methyl[2-(3-methyl-1,2,4-oxadiazol-5-yl)phenyl]
carbamate, Hydrochloride A mixture of [4-methoxy-2-(3-methyl-1,2,4-oxadiazol-5-yl)phenyl]carbamoyl chloride (500 mg) and N-[2-[4-(hydroxymethyl)-1-piperidinyl]ethyl]methanesulphonamide (662 mg) was heated at 150° under nitrogen for 20 min. FCC with System A (250:10:1) as the eluent gave a pale yellow solid (380 mg). This material was dissolved in dichloromethane:ethanol (1:1; 5 ml) and treated with an excess of ethereal hydrogen chloride solution. The solvent was removed in vacuo and the residue triturated with dry ether (5×5 ml) to give the title compound as a white solid (400 mg), m.p. 200°.

T.l.c. (System A, 250:10:1) Rf=0.35

EXAMPLE 12

[1-[2-[(Methylamino)sulphonyl]ethyl]-4-piperidinyl]
methyl[2-(3-methyl-1,2,4-oxadiazol-5-yl)phenyl]
carbamate Maleate (1:1)

4-Piperidinylmethyl[2-(3-methyl-1,2,4-oxadiazol-5-yl)phenyl]carbamate (442 mg), acetonitrile (25 ml), N-methylethenesulphonamide, (172 mg) and N,N-diisopropylethylamine (0.49 ml) were stirred at reflux under nitrogen for 4 h. The solvent was removed under vacuum to leave a brown oil (800 mg). FCC using System A (200:8:1) as eluant gave a white solid (303 mg). The free base was dissolved in boiling ethyl acetate (5 ml). A solution of maleic acid (86 mg) in warm ethyl acetate (4 ml) was added. On standing a white solid precipitated. This was collected by filtration and dried in vacuo to give the title compound as a white powder, (394 mg), m.p. 181°–182°.

T.l.c. (System A, 200:8:1) Rf 0.45

Similarly prepared:

EXAMPLE 13

[1-(2-Methoxyethyl)-4-piperidinyl]methyl[2-(3-methyl-1,2,4-oxadiazol-5-yl)phenyl]carbamate Maleate
(1:1) (289 mg), m.p. 124°–126°, Analysis: C,56.6; H,5.97; N,11.38;

$C_{19}H_{26}N_4O_4.C_4H_4O_4$ requires: C,56.43; H,6.27; N,11.45%

From 4-Piperidinylmethyl [2-(3-methyl-1,2,4-oxadiazol-5-yl)phenyl]carbamate (366 mg) and 2-bromoethylmethyl ether (0.11 ml).

EXAMPLE 14

[1-[3-[(Methylsulphonyl)amino]propyl]-4-piperidinyl]methyl[2-(3-methyl-1,2,4-oxadiazol-5-yl)phenyl]carbamate Maleate (1:1) (308 mg), m.p.
161°–162°.

Analysis Found: C,49.94; H,5.87; N,12.2;

$C_{20}H_{26}N_5O_5S.C_4H_4O_4.0.1H_2O$ requires: C,50.62; H,5.88; N,12.30%

Water determination, shows 0.32% w/w $H_2O$ ~0.1 molar equivalents $H_2O$

From 4-Piperidinylmethyl [2-(3-methyl-1,2,4-oxadiazol-5-yl)phenyl]carbamate (256 mg) and N-(3-bromopropyl) methane Sulphonamide (216 mg).

EXAMPLE 15

[1-[2-(Acetylamino)ethyl]-4-piperidinyl]methyl[2-
(3-methyl-1,2,4-oxadiazol-5-yl)phenyl]carbamate
di-p-toluoyl-1-tartrate From 4-Piperidinylmethyl [2-(3-methyl-1,2,4-oxadiazol-5-yl)phenyl]carbamate (304 mg) and N-(2-chloroethyl)acetamide (0.1 ml). The free base (74 mg) was dissolved in boiling ethyl acetate (5 ml). A solution of maleic acid (29 mg) was added. On standing no precipitation occurred. The free base was reliberated by the addition of 8% sodium bicarbonate solution (20 ml), extraction with dichloromethane (4×10 ml), drying the combined organic layers and concentrating in vacuo to give a white solid (ca. 0.1 g). This was purified by chromatography on silica using System A (200:8:1) as eluant to give the free base as a white powder, (70 mg). The free base (53 mg) was dissolved in methanol (5 ml). A solution of di-p-toluoyl-l-tartaric acid (51 mg) was added. The solution was evaporated to dryness and the glassy residue triturated with diethyl ether (20 ml). Filtration and drying under vacuum gave the title compound as a white solid (75 mg), m.p. >130° (dec.)

Analysis found: C,60.21; H,5.91; N,8.59;

$C_{20}H_{27}N_5O_4.C_{20}H_{18}O_8.H_2O.0.1C_4H_{10}O$ requires: C,59.67; H,5.95; N,8.61% Water determination, shows 2.29% w/w $H_2O$ ~1.0 molar equivalents $H_2O$

EXAMPLE 16

N-[2-[4-[2-[[[[2-(3-Methyl-1,2,4-oxadiazol-5-yl)phenyl]amino]carbonyl]amino]ethyl]-1-piperidinyl]ethyl]methanesulphonamide Dihydrochloride From N-[2-(3-methyl-1,2,4-oxadiazol-5-yl)phenyl]-N'-[2-(4-piperidinyl)ethyl urea 300 mg) and 2-iodoethyl-N-methylsulphonamide (341 mg). The free base (215 mg) was dissolved in dichloromethane (2 ml) and treated with an excess of ethereal hydrogen chloride solution. The solvent was removed in vacuo and the residue triturated with dry ether (5×10 ml) to give the title compound as a pale yellow solid (200 mg) m.p. 178°–180°

T.l.c. (System A, 150:10:1) Rf 0.28

EXAMPLE 17

1-[2-[(Methylsulphonyl)amino]ethyl]-4-piperidinyl [2-(3-methyl-1,2,4-oxadiazol-5-yl)phenyl]carbamate Monohydrochloride From 2-(3-methyl-1,2,4-oxadiazol-5-yl)-4-(piperidinyl) [2-(3-methyl-1,2,4-oxadiazol-5-yl)phenyl]carbamate (350 mg) and 2-iodoethyl-N-methylsulphonamide (433 mg). The free base (360 mg) was dissolved in dichloromethane (3 ml) and treated with an excess of ethereal hydrogen chloride solution. The solvent was removed in vacuo and the residue triturated with dry ether (5×10 ml) to give the title compound as a white solid (370 mg), m.p. 219°–220°

T.l.c. (System A, 250:10:1), Rf 0.30.

EXAMPLE 18

[1-(3-Amino-3-oxopropyl)-4-piperidinyl]methyl[2-(3-methyl-1,2,4-oxadiazol-5-yl)phenyl]carbamate Maleate (1:1)

4-Piperidinylmethyl [2-(3-methyl-1,2,4-oxadiazol-5-yl)phenyl]carbamate (410 mg), 3-chloropropionamide (142 mg), N,N-diisopropylethylamine (0.48 ml) and dry acetonitrile (20 ml) were stirred at reflux under nitrogen for 25 h. Cooling and concentration in vacuo gave an orange solid (0.612 g) which was purified by FCC using System A (90:10:1) as eluant to give a white solid (399 mg). The free base was dissolved in boiling ethyl acetate (20 ml). A solution of maleic acid (119 mg) in hot ethyl acetate (3 ml) was added. Concentration in vacuo followed by trituration of the residue in tetrahydrofuran (20 ml), filtration and drying gave a brown solid (378 mg) which was again triturated with tetrahydrofuran (15 ml). Filtration and drying in vacuo gave a white solid (312 mg). Recrystallisation from tetrahydrofuran (10 ml) and ethanol (3.5 ml) gave, on standing and after addition of cyclohexane (ca. 5 ml), the title compound as white crystals, (255 mg).

Analysis Found: C,54.47; H,6.33; N,12.39;

$C_{19}H_{25}N_5O_4.C_4H_4O_4$ requires: C,54.86; H,5.81; N,13.91%

Water analysis, shows 0.95% w/w $H_2O$ ~0.27molar equivalents.

The title compound was cleaved by 8% sodium bicarbonate solution (15 ml) and the free base isolated by extracting the aqueous layer with dichloromethane (4×10 ml), drying the combined organic layers and concentrating in vacuo to give a white solid (158 mg). This was dissolved in warm ethyl acetate (10 ml). A solution of maleic acid (50 mg) in hot tetrahydrofuran (1 ml) was added. The resulting solution was concentrated in vacuo to give an oil which was triturated with tetrahydrofuran to give a white solid. This was filtered, washed with cyclohexane and dried under vacuum to give a white solid (143 mg). N.m.r. showed ca. 1 molar equivalent of tetrahydrofuran. To remove residual tetrahydrofuran, the salt was triturated with diethyl ether (20 ml). Filtration, washing with cyclohexane and drying under vacuum gave a white solid (97 mg) M.p. 138°–139°

Analysis Found: C,55.32; H,5.97; N,13.93;

$C_{19}H_{25}N_5O_4.C_4H_4O_4$ requires: C,54.86; H,5.81; N,13.91%

EXAMPLE 19

[1'-(Methylsulphonyl)[1,4'-bipiperidin]-4-yl]methyl [2-(3-methyl-1,2,4-oxadiazol-5-yl)phenyl]carbamate Maleate (1:1)

To 4-Piperidinylmethyl [2-(3-methyl-1,2,4-oxadiazol-5-yl)phenyl]carbamate (366 mg) was added N-(4-oxopiperidinyl)methanesulphonamide (180 mg), dichloroethane (15 ml) and glacial acetic acid (0.07 ml). The yellow solution was stirred under nitrogen and sodium triacetoxyborohydride (355 mg) cautiously added. The resulting suspension was stirred under nitrogen for 48 h and another quantity of the borohydride (156 mg) added. After stirring for a further 24 h, 8% sodium bicarbonate solution (25 ml) was added. The layers were separated and the aqueous layer extracted with dichloromethane (5×10 ml). The combined organic extracts were dried and concentrated in vacuo to give a cream solid (604 mg), which was purified by FCC using System A (30:8:1) as eluant to give a white solid (249 mg). This was further purified by FCC using System A (200:8:1) as eluant to give a white solid (185 mg) which was further purified on silica using ethyl acetate:ethanol:aqueous ammonia (100:8:1) as eluant to give the free base of the title compound as a white solid, (54 mg).

T.l.c. (System A, 30:8:1) Rf 0.36

The free base was dissolved in boiling ethyl acetate (ca. 3 ml). Maleic acid (13.7 mg) was added and the mixture left standing overnight. Filtration, washing with fresh ethyl acetate (5 ml) and drying in vacuo gave the title compound (36 mg), m.p. 186°–187°

Analysis Found: C,52.11; H,5.9; N,11.51, $C_{22}H_{32}N_5O_5S.0.95C_4H_4O_4.0.04H_2O$ requires: C,52.56; H,6.13; N,11.88%

Water analysis found: 0.12% w/w $H_2O$ ~0.04 molar equivalents $H_2O$

EXAMPLE 20

[1-[2-[(Methylsulphonyl)amino]ethyl]-4-piperidinyl]
methyl[5-fluoro-2-(3-methyl-1,2,4-oxadiazol-5-
yl)phenyl]carbamate Maleate (1:1)

A solution of 5-fluoro-2-(3-methyl-1,2,4-oxadiazol-5-yl) benzenamine (971 mg) in sieve-dried acetonitrile (15 ml) was added dropwise to a solution of phosgene at 0° (20% in toluene, 14 ml). The white suspension was stirred under $N_2$ for 5 h. Concentration in vacuo gave a white solid, to which was added dry dichloromethane (30 ml) followed by a solution of N-[2-[4-(Hydroxymethyl)-1-piperidinyl]ethyl] methanesulphonamide (1.615 g) in sieve-dried dichloromethane (30 ml). The resulting suspension was stirred under nitrogen at room temperature for 24 h. 8% sodium bicarbonate (60 ml) was added and the layers separated. The aqueous layer was extracted with dichloromethane (4×10 ml). The combined organic layers were dried, filtered and concentrated in vacuo to give a white foam (1.9 g). FCC using System A (200:8:1) as eluant produced a white solid (0.35 g), which was further purified by FCC using ethyl acetate:ethanol:aqueous ammonia (200:8:1) as eluant to give the free base of the the title compound, as a white powder (173 mg).

T.l.c. (System A, 200:8:1) Rf 0.25

The free base was dissolved in boiling ethyl acetate (5 ml) and a solution of maleic acid (47 mg) in warm ethyl acetate (3 ml) was added. Standing, filtration and drying under vacuum gave the title compound as a white solid (168 mg), m.p. 165°–167°.

Analysis Found: C,48.16; H,5.25; N,12.19;

$C_{19}H_{26}FN_5O_5S.C_4H_4O_4$ requires: C,48.33; H,5.29; N,12.25%

EXAMPLE 21

N-[2-[4-[[[[[2-(3-methyl-1,2,4-oxadiazol-5-yl)phe-
nyl]amino]carbonyl]amino]methyl]-1-piperidinyl]
ethyl]methanesulphonamide Maleate (1:1)

A solution/suspension of [2-(3-Methyl-1,2,4-oxadiazol-5-yl)phenyl]carbamoyl chloride (129 mg) in acetonitrile (30 ml) was stirred at room temperature under a nitrogen atmosphere. N-[2-[4-(aminomethyl)-1-piperidinyl]ethyl]methanesulphonamide (140 mg) was added in acetonitrile (5 ml) and the resulting solution stirred overnight. The resulting white suspension was reduced to dryness under vacuo before purifying by FCC with System A (90:10:1) as the eluent, giving the free base of the title compound as a white solid (61 mg). T.l.c. (System A, 90:10:1) Rf 0.38. The free base was dissolved in methanol (5 ml) and maleic acid (15 mg), in methanol (3 ml) was added. The solvent was removed in vacuo and the residual oil was triturated with ether to yield a the title compound as a white solid (74 mg) 67°–69°.

Analysis Found: C,48.77; H,5.94; N,14.6;

$C_{19}H_{28}N_6O_4S.C_4H_4O_4.H_2O$ requires: C,48.41; H,6.01; N, 14.73%

EXAMPLE 22

[1-[2-[(Methylsulphonyl)amino]ethyl]-4-piperidinyl]
methyl[2-(3-cyclopropyl-1,2,4-oxadiazol-5-yl)phe-
nyl]carbamate Maleate (1:1)

Sodium hydride (60% in oil; 73 mg) was added to a solution of 2-cyclopropylacetamide oxime (146 mg) in distilled tetrahydrofuran (20 ml) containing 4 molecular sieves (6 pellets) under a nitrogen atmosphere at room temperature. The yellow suspension was refluxed for 0.75 h, cooled and a further portion of sodium hydride (68 mg) added, followed by a solution of methyl-2-[[[[1-[2-[(methylsulphonyl)amino]ethyl]-4-piperidinyl]methoxy]carbonyl] amino]benzoate (231 mg) in distilled tetrahydrofuran (10 ml). The solution was refluxed for 4.5 h, then allowed to cool. Ethanol (10 ml) was added and the resulting suspension concentrated in vacuo to give a yellow solid. FCC using System A (200:8:1) as eluant gave the free base of the title compound (40 mg).

T.l.c. (System A, 200:8:1) Rf 0.25.

The free base was dissolved in warm ethyl acetate (2 ml) and a solution of maleic acid (13 mg) in warm ethyl acetate (2 ml) was added. The resulting precipitate was collected by filtration and dried in vacuo to give the title compound as a yellow powder, (43 mg), m.p. 160°–161°.

Analysis Found: C,51.42; H,5.74; N,11.89

$C_{21}H_{29}N_5O_5S.C_4H_4O_4$ requires: C,51.8; H,5.74; N,12.08%

Similarly prepared:

EXAMPLE 23

[1-[2-[(Methylsulphonyl)amino]ethyl]-4-piperidinyl]
methyl[2-(3-phenyl-1,2,4-oxadiazol-5-yl)phenyl]
carbamate Maleate (1:1), (59 mg), m.p. 169°–170°.

Analysis Found: C,54.29; H, 5.53; N,10.77;

$C_{24}H_{29}N_5O_5S.C_4H_4O_4.0.3H_2O$ requires: C,54.15; H,5.45; N,11.28%

Water determination Found: 0.86% w/w $H_2O$, ~0.3 molar equivalents $H_2O$.

From benzamide oxime (92 mg) and methyl-2-[[[[1-[2-[(methylsulphonyl)amino]ethyl]-4-piperidinyl]methoxy] carbonyl]amino]benzoate (167 mg). Via free base of title compound (60 mg)

T.l.c. (System A, 200:8:1) Rf 0.3.

EXAMPLE 24

[1-[2-[(Methylsulphonyl)amino]ethyl]-4-piperidinyl]
methyl[2-[3-(1-1,2,4-oxadiazol-5-yl]phenyl]carbam-
ate Maleate (1:1) (126 mg), m.p. 171°–172°;

Analysis Found: C,51.01; H,6.04; H,11.76;

$C_{21}H_{31}N_5O_5S.C_4H_4O_4.0.1H_2O$ requires: C,51.47; H,6.08; N,12.00%

Water determination, found 0.27% $H_2O$ ~0.1 molar equivalents $H_2O$

From N-hydroxy-2-methylpropanimidamide (102 mg) and methyl-2-[[[[1-[2-[( methylsulphonyl)amino]ethyl]-4-piperidinyl]methoxy ]carbonyl]amino]benzoate (230 mg). Via the free base (124 mg).

T.l.c. (System A, 200:8:1) Rf 0.3

EXAMPLE 25

[1-[2-[(Methylsulphonyl)amino]ethyl]-4-piperidinyl]
methyl[2-[3-(phenylmethyl)-1,2,4-oxadiazol-5-yl]
phenyl]carbamate Maleate (1:1) (65 mg) m.p.
143°–144°.

Analysis Found: C,54.7; H,5.5; N,10.95;

$C_{25}H_{31}N_5O_5S.C_4H_4O_4.0.15H_2O$ requires: C,55.1; H,5.62; N,11.08%

Water determination showed ca. 0.40% w/w

~0.15 molar equivalents present

From 2-phenylacetamideoxime (120 mg) methyl-2-[[[[1-[2-[(methylsulphonyl)amino]ethyl]-4-piperidinyl]methoxy]carbonyl]amino]benzoate (253 mg). Via free base (80 mg).

EXAMPLE 26

1-[2-[(Methylsulphonyl)amino]ethyl]-4-piperidinyl] methyl[2-(3-methyl-1,2,4-oxadiazol-5-yl)phenyl] carbamate From acetamide oxime (22 mg) and methyl-2-[[[[1-[2-[(methylsulphonyl)amino]ethyl]-4-piperidinyl]methoxy]carbonyl]amino]benzoate (100 mg) to give free base (52 mg) as a white solid. (Characterisation as for Example 1).

EXAMPLE 27

[1-[2-[(Methylsulphonyl)amino]ethyl]-4-piperidinyl] methyl][2-[3-(1,1-dimethylethyl)-1,2,4-oxadiazol-5-yl]phenyl]carbamate Monohydrochloride From N-hydroxy-2,2-dimethylpropanimidamide (85 mg) and methyl-2-[[[[1-[2-[(methylsulphonyl)amino]ethyl]-4-piperidinyl]methoxy]carbonyl]amino]benzoate (250 mg) to give free base as a cream solid (144 mg)

T.l.c (System A, 95:5:0.5)

The free base was dissolved in dichloromethane (5 ml) and treated with ethereal hydrochloric acid. Concentration and trituration with ether afforded the title compound as a cream solid (120 mg), m.p. 233°–235°

Analysis Found: C,51.0; H,6.7; N,13.5; $C_{22}H_{33}N_5O_5S.HCl$

Requires: C,51.2; H,6.7; N,13.6%

Water analysis contains 0.35% $H_2O$ by weight.

EXAMPLE 28

[1-(1-Methylethyl)-4-piperidinyl]methyl[2-(3-methyl-1,2,4-oxadiazol-5-yl)phenyl]carbamate N-[2-(3-methyl-1,2,4-oxadiazol-5-yl)phenyl]-N'-[2-(4-piperidinyl)ethyl]urea (450 mg) (287 mg), analar grade acetone (0.075 ml) and glacial acetic acid (0.07 ml) were stirred in dichloromethane (20 ml) under nitrogen. Sodium triacetoxyborohydride (269 mg) was cautiously added. The cloudy liquid was stirred and after 49 h a further quantity of acetone (0.05 ml) was added. After 68 h sodium triacetoxyborohydride (100 mg) was added. After 120 h 8% sodium bicarbonate solution was added. The resulting layers were separated and the aqueous layer extracted with dichloromethane (4×10 ml). The combined organic layers were concentrated to give a white solid (244 mg). This was purified by FCC using System A (90:10:1), yielding the title compound as a white powder (130 mg).

T.l.c. (System A 90:10:1) Rf 0.55.

EXAMPLE 29

[1-(1-Methylethyl)-4-piperidinyl]methyl[2-(3-methyl-1,2,4-oxadiazol-5-yl)phenyl]carbamate Maleate (1:1)

To a warm solution of [1-(1-methylethyl)-4-piperidinyl] methyl[2-(3-methyl-1,2,4-oxadiazol-5-yl)phenyl]carbamate (120 mg) in the minimum amount of ethyl acetate was added a solution of maleic acid (36.9 mg) in the minimum amount of warm methanol (2 ml). Concentration in vacuo left a white oily residue which was triturated twice in ether (10 ml). The resulting white powder was filtered and dried in vacuo to yield the title compound as a light brown solid (107 mg), m.p. 89°–93°.

Analysis Found: C,57.39; H,6.41; N,11.2; $C_{19}H_{26}N_4O_3.C_4H_4O_4.2C_4H_{10}O.0.35H_2O$ requires: C,57.68; H,6.65: N,11.3

Water analysis found 0.71% w/w $H_2O$ (i.e. ca. 0.2 molar equivalents $H_2O$)

EXAMPLE 30

1-Methyl-4-[[[[[2-(3-methyl-1,2,4-oxadiazol-5-yl)phenyl]amino]carbonyl]oxy]methyl]-1-[2-[(methylsulphonyl)amino]ethyl]piperidinium Iodide

[1-[2-[(Methylsulphonyl)amino]ethyl]-4-piperidinyl]methyl[2-(3-methyl-1,2,4-oxadiazol-5-yl)phenyl]carbamate (136 mg) was dissolved in sieve-dried dichloromethane (3 ml). Methyl iodide (0.9 ml) was added and the solution stirred for 48 h. The resulting white residue was triturated with cyclohexane (10 ml) and dried in vacuo to give a white solid (145 mg). Trituration with ethyl acetate (3×10 ml) gave, on filtration and drying in vacuo, the title compound as a white solid (104 mg), 190° (dec.).

Analysis Found: C,41.13; H,5.24; N,11.88;

$C_{20}H_{30}IN_5O_5S$ requires: C,41.46; H,5.22; N,11.68%

EXAMPLE 31

[1-[2-[(Methylsulphonyl)amino]ethyl]-4-piperidinyl] methyl[2-(3-methyl-1,2,4-oxadiazol-5-yl)phenyl] carbamate N-oxide

[1-[2-[(Methylsulphonyl)amino]ethyl]-4-piperidinyl]methyl[2-(3-methyl-1,2,4-oxadiazol-5-yl)phenyl]carbamate(600 mg) was dissolved in 8% sodium bicarbonate solution, and the free base extracted with dichloromethane (4×10 ml). Concentration in vacuo gave a white solid (460 mg). To this was added a further portion of the free base (136 mg). The combined free base was dissolved in sieve-dried chloroform (25 ml), m-chloroperbenzoic acid (589 mg) was cautiously added and the resulting suspension stirred under nitrogen for 20 h at room temperature. 2N hydrochloric acid (30 ml) was added. The layers were separated, the aqueous layer washed with chloroform (2×30 ml) and the combined organic layers back-extracted with water (10 ml). The combined aqueous layers were concentrated in vacuo to give a white solid (0.675 g). FCC using System A (25:8:1) as eluant gave a solid which was further purified by FCC using System A (50:8:1) as eluant to give the title compound as a white powder (270 mg), m.p. >185° (dec).

Mass spectrum shows $[MH]^+$ at 454.2

T.l.c. (System A, 25:8:1) Rf 0.4.

EXAMPLE 32

N-[2-[4-[[[[[2-(5-Methyl-1,2,4-oxadiazol-3-yl)phenyl]amino]carbonyl]amino]methyl]-1-piperidinyl] ethyl]methanesulphonamide Monohydrochloride A solution of N-[2-[4-(aminomethyl)-1-piperidinyl]ethyl] methanesulphonamide (270 mg) in acetonitrile (10 ml) was added to a stirred solution of [2-(5-methyl-1,2,4-oxadiazol-3-yl)phenyl]carbamoyl chloride (250 mg) in acetonitrile (30 ml) and stirred at room temperature under a nitrogen atmosphere for 22 h and then at 60° for 22 h. The reaction mixture was then concentrated to give a cream solid (490 mg) The solid was purified by FCC eluting with ethyl acetate followed by System A (90:10:1) to yield a cream solid (66 mg). This was dissolved in methanol and ethereal hydrogen chloride was added. Concentration followed by trituration with ethyl acetate gave a solid which was further purified by FCC using System A (90:10:1) as eluant. The resulting solid (32 mg) was dissolved in dichloromethane/methanol, treated with ethereal hydrogen chloride and triturated with ethyl acetate to give the title compound as a white solid (12 mg).

N.m.r. □ (DMSO) 4.65 (1H, brs), 8.885 (1H, s), 8.275 (1H, brd) 7.975 (1H, brd) 7.42–7.505 (2H, dt & t), 7.375 (1H, brt), 7.125(1H, dt), 3.525 (2H, brd) 2.8–3.45 (11H 3×m), 1.865 (2H, brd), 1.75 (1H, brm) 1.455 (2H, brq).

EXAMPLE 33

[1-[2-[(Methylsulphonyl)methylamino]ethyl]-4-piperidinyl]methyl-[2-(3-methyl-1,2,4-oxadiazol-5-yl)phenyl]carbamate Maleate (1:1)

To a stirred solution of [1-[2-[(methylsulphonyl)amino]ethyl]-4-piperidinyl]methyl[2-(3-methyl-1,2,4-oxadiazol-5-yl)phenyl]carbamate (190 mg) in dry tetrahydrofuran (5 ml) was added tetrabutylammonium fluoride (1.10 ml, 1.0M solution in tetrahydrofuran). After 30 min methyl iodide (0.03 ml) was added and the suspension stirred for 2.5 h. Pouring into 8% sodium bicarbonate (25 ml) solution, extracting with dichloromethane (4×10 ml) and drying the combined organic layers gave, on filtration and concentration in vacuo, a yellow solid (0.414 g). FCC using System A (200:8:1) as eluant gave a white solid (224 mg). Further purification by FCC using System A (300:8:1) as eluant gave a white solid (144 mg). Further FCC using System A (400:8:1) gave the free base of the title compound as a white solid (55 mg).

T.l.c (System A 300:8:1) Rf 0.35

The free base (55 mg) was dissolved in boiling ethyl acetate (1 ml) and maleic acid (17 mg) in hot ethyl acetate (1 ml) added. White crystals precipitated. These were filtered and dried under vacuum to give the title compound as a white powder (51 mg), m.p. 170°–172°.

Analysis Found: C,50.77; H,5.911 N,12.21;

$C_{20}H_{29}N_5O_5 \cdot C_4H_4O_4$ requires: C,50.78; H,5.86; N,12.34%

EXAMPLE 34

N-(3-Methyl-1,2,4-oxadiazol-5-yl)-N'-[2-[1-(phenylmethyl)-4-piperidinyl]ethyl]urea A mixture of [2-(3-methyl-1,2,4-oxadiazol-5-yl)phenyl] carbamoyl chloride (1.0 g) and 4-(2-aminoethyl)-1-benzylpiperidine (1.38 g) was stirred at 150° under nitrogen for 15 min. FCC with System A (250:10:1) as the eluent gave the title compound as a white solid (1.47 g) m.p. 138°–9°

T.l.c. (System A 250:10:1), Rf=0.42

Similarly prepared:

EXAMPLE 35

1-(Phenylmethyl)-4-piperidinyl[2-(3-methyl-1,2,4-oxadiazol-5-yl)phenyl]carbamate (1.18 g)

T.l.c. (System a 500:10:1) Rf=0.50

From [2-(3-Methyl-1,2,4-oxadiazol-5-yl)phenyl]carbamoyl chloride (1.0 g) and 1-benzyl-4-hydroxypiperidine (1.2 g). A sample of the free-base (160 mg) was dissolved in dry dichloromethane (2 ml) and treated with an excess of ethereal hydrogen chloride solution. The solvent was removed in vacuo and the residue triturated with dry ether (5×5 ml) to give the monohydrochloride of the title compound as a white solid (163 mg), m.p. 240°–242°

Analysis Found: C.61.2; H,6.0; N,12.8;

$C_{22}H_{24}N_4O_3 \cdot HCl$ requires: C,61.6; H,5.9; N,13.1%

EXAMPLE 36

[1-[(phenylmethyl)-4-piperidinyl]methyl[2-(3-methyl-1,2,4-oxadiazol-5-yl)phenyl]carbamate A solution/suspension of [2-(3-methyl-1,2,4-oxadiazol-5-yl)phenyl]carbamoyl chloride (1.177 g) in acetonitrile (50 ml) was stirred under a nitrogen atmosphere. 1-benzyl-4-hydroxymethyl piperidine (1.53 g) in dry dichloromethane (5 ml) was added and the resulting solution stirred at room temperature overnight. The mixture was reduced to dryness under vacuo to give a white solid (3.71). The solid was washed with 2N hydrochloric acid (100 ml) and extracted with ether (2×100 ml). The aqueous was are-basified with sodium bicarbonate (pH8) and the product extracted into dichloromethane (3×500 ml). The solvent was removed under vacuo yielding a white solid which was further purified by FCC with 15% methanol in toluene as eluent, giving the title compound as a pale yellow solid (1.53 g), m.p. 105°–107°.

T.l.c. (15% methanol in toluene) Rf 0.74

EXAMPLE 37

[1-[2-(Methylsulphonyl)amino]ethyl]-4-piperidinyl] methyl[2-(3-methyl-1,2,4-oxadiazol-5-yl)phenyl] carbamate Methanesulphonyl chloride (0.02 ml) was added to a stirred solution of 1-[(2-aminoethyl-4-piperidinyl]methyl[2-(3-methyl-1,2,4-oxadiazol-5-yl)phenyl]carbamate (100 mg) and pyridine (0.05 ml) in dry dichloromethane (2.5 ml) under nitrogen. After 1.5 h water (10 ml) was added and the mixture extracted with dichloromethane (3×5 ml). The combined extracts were dried, filtered and evaporated to give a yellow oil (~125 mg). FCC with System A (250:10:1) as the eluent gave the title compound as a white solid (68 mg) m.p. 126°–7°.

The following salt was prepared according to conventional procedures:

EXAMPLE 38

[1-[2-(Methylsulphonyl)amino]ethyl]-4-piperidinyl] methyl[2-(3-methyl-1,2,4-oxadiazol-5-yl)phenyl] carbamate Methanesulphonate Salt m.p. 165°–167°, $v_{max}$ (Nujol) 1741, 1597, 1044, 748, 552 cm$^{-1}$.

BIOLOGICAL DATA

The antagonism of 5-HT at 5-HT$_4$ receptors by compounds of the invention has been demonstrated in vitro using the rat oesophagus test as described hereinbefore. Thus, for example, the compounds of the following examples gave the following pkb values

| Compound of Example | pkb |
|---|---|
| 1 | 10.8 |
| 11 | 8.1 |
| 13 | 10.0 |
| 20 | 8.9 |
| 21 | 7.8 |
| 33 | 8.6 |

The compounds of the invention exhibited no apparent adverse or toxic effects widen administered to rats in vivo. Thus the compound of Example 1 exhibited no apparent adverse or toxic effects when administered intraperitoneally to conscious rats up to doses of 1 mg/kg.

PHARMACY EXAMPLES

Example 1—Tablets

| a) Compound of the invention | 5.0 mg |
|---|---|
| Lactose | 95.0 mg |
| Microcrystalline Cellulose | 90.0 mg |
| Cross-linked polyvinylpyrrolidone | 8.0 mg |
| Magnesium Stearate | 2.0 mg |
| Compression weight | 200.0 mg |

The compound of the invention, microcrystalline cellulose, lactose and cross linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| b) Compound of the invention | 5.0 mg |
|---|---|
| Lactose | 165.0 mg |
| Pregelatinised Starch | 20.0 mg |
| Cross-linked polyvinylpyrrolidone | 8.0 mg |
| Magnesium Stearate | 2.0 mg |
| Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

Example 2—Capsules

| a) Compound of the invention | 5.0 mg |
|---|---|
| Pregelatinised Starch | 193.0 mg |
| Magnesium Stearate | 2.0 mg |
| Fill weight | 200.0 mg |

The compound of the invention and pregelatinised starch are screened through a 500 micron mesh sieve, blended together and lubricated with magnesium stearate, (meshed through a 250 micron sieve). The blend is filled into hard gelatine capsules of a suitable size.

| b) Compound of the invention | 5.0 mg |
|---|---|
| Lactose | 177.0 mg |
| Polyvinylpyrrolidone | 8.0 mg |
| Cross-linked polyvinylpyrrolidone | 8.0 mg |
| Magnesium Stearate | 2.0 mg |
| Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

Example 3—Syrup

| a) Compound of the invention | 5.0 mg |
|---|---|
| Hydroxypropyl Methylcellulose | 45.0 mg |
| Propyl Hydroxybenzoate | 1.5 mg |
| Butyl Hydroxybenzoate | 0.75 mg |
| Saccharin Sodium | 5.0 mg |
| Sorbitol Solution | 1.0 ml |
| Suitable Buffers | qs |
| Suitable flavours | qs |
| Purified Water to | 10. ml |

The hydroxypropyl methylcellulose is dispersed in a portion of hot purified water together with the hydroxybenzoates and the solution is allowed to cool to room temperature. The saccharin sodium flavours and sorbitol solution are added to the bulk solution. The compound of the invention is dissolved in a portion of the remaining water and added to the bulk solution. Suitable buffers may be added to control the pH in the region of maximum stability. The solution is made up to volume, filtered and filled into suitable containers.

Example 4—Injection Formulation

| | % w/v |
|---|---|
| Compound of the invention | 1.00 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

I claim:
1. A compound of formula (I)

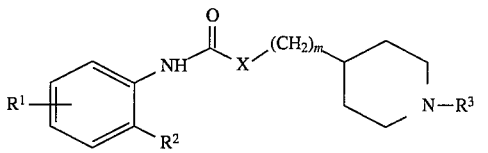

wherein $R^1$ represents a hydrogen or a halogen atom, or a $C_{1-6}$alkyl, $C_{1-6}$alkoxy or hydroxy group;
$R^2$ represents an oxadiazole or thiadiazole ring substituted by a group selected from $C_{1-6}$alkyl, $C_{3-7}$cycloalkyl, —$CH_2C_{2-5}$alkenyl, —$CH_2CH_{2-5}$alkynyl, phenyl or benzyl;
X represents an oxygen atom;
m represents zero, 1 or 2;
$R^3$ represents $C_{1-6}$alkyl, benzyl, —$(CH_2)_nR^4$ or
$R^4$ represents a group selected from cyano, hydroxyl, $C_{1-6}$alkoxy, phenoxy, $C(O)C_{1-6}$alkyl, $C(O)C_6H_5$, —$CONR^6R^7$, $NR^6COR^7$, —$SO_2NR^6R^7$ or —$NR^6SO_2R^7$ (wherein each of $R^6$ and $R^7$ independently represent a hydrogen atom, a $C_{1-6}$alkyl or phenyl group);
n represents 2 or 3;
$R^5$ represents $COR^8$ or $SO_2R^8$ (wherein $R^8$ represents a hydrogen atom, a $C_{1-6}$alkyl or phenyl group);
and quaternary ammonium derivatives having the formula

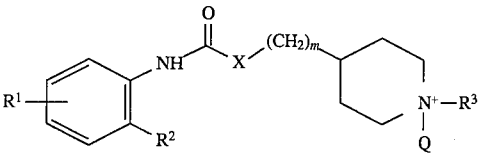

where Q represents $C_{1-6}$alkyl, piperidine N-oxides of said compound of formula (I) and pharmaceutically acceptable salts and solvates thereof.
2. A compound as claimed in claim 1 in which m is 1.
3. A compound as claimed in claim 1 in which $R^3$ is a group —$(CH_2)_nR^4$.
4. A compound as claimed in claim 3 in which n is 2.
5. A compound a claimed in claim 3 in which $R^4$ is a group $NR^6SO_2R^7$.
6. A compound as claimed in claim 4 in which $R^4$ is a group $NR^6SO_2R^7$.
7. [1-[2-[(Methylsulphonyl)methylamino]ethyl]-4-piperidinyl]methyl[2-(3-methyl-1,2,4-oxadiazol-5-yl) phenyl]carbamate;
[1-[2-[(Methylsulphonyl)amino]ethyl]-4-piperidinyl]methyl[2-(3-methyl-1,2,4-thiadiazol-5-yl)phenyl]carbamate;
[1-[2-(Methylsulphonyl)amino]ethyl]-4-piperidinyl]methyl[4-methyl-2-(3-methyl-1,2,4-oxadiazol-5-yl)phenyl]carbamate;
[1-[2-[(Methylamino)sulphonyl]ethyl]-4-piperidinyl]methyl[2-(3-methyl-1,2,4-oxadiazol-5-yl)phenyl]carbamate;
[1-(2-Methoxyethyl)-4-piperidinyl]methyl[2-(3-methyl-1,2,4-oxadiazol-5-yl)phenyl]carbamate;
[1-[3-[(Methylsulphonyl)amino]propyl]-4-piperidinyl]methyl[2-(3-methyl-1,2,4-oxadiazol-5-yl)phenyl]carbamate;
[1-[2-(Acetylamino)ethyl]-4-piperidinyl]methyl[2-(3-methyl-1,2,4-oxadiazol-5-yl)phenyl]carbamate di-p-toluoyl-1-tartrate;
N-[2-[4-[2-[[[[2-(3-Methyl-1,2,4-oxadiazol-5-yl)phenyl]amino]carbonyl]amino]ethyl]-1-piperidinyl]ethyl]methanesulphonamide;
1-[2-[(Methylsulphonyl)amino]ethyl]-4-piperidinyl [2-(3-methyl-1,2,4-oxadiazol-5-yl)phenyl]carbamate;
[1-(3-Amino-3-oxopropyl)-4-piperidinyl]methyl[2-(3-methyl-1,2,4-oxadiazol-5-yl)phenyl]carbamate;
[1'-(Methylsulphonyl)[1,4'bipiperidin]-4-yl]methyl[2-(3-methyl-1,2,4-oxadiazol-5-yl)phenyl]carbamate;
[1-[2-[(Methylsulphonyl)amino]ethyl]-4-piperidinyl]methyl[5-fluoro-2-(3-methyl-1,2,4-oxadiazol-5-yl)phenyl]carbamate;
N-[2-[4-[[[[2-(3-Methyl-1,2,4-oxadiazol-5-yl)phenyl]amino]carbonyl]amino]methyl]-1-piperidinyl]ethyl]methanesulphonamide;
[1-[2-[(Methylsulphonyl)amino]ethyl]-4-piperidinyl]methyl[2-(3-cyclopropyl-1,2,4-oxadiazol-5-yl)phenyl]carbamate;
[1-[2-[(Methylsulphonyl)amino]ethyl]-4-piperidinyl]methyl[2-(3-phenyl-1,2,4-oxadiazol-5-yl)phenyl]carbamate;
[1-[2-[(Methylsulphonyl)amino]ethyl]-4-piperidinyl]methyl[2-[3-(1-methylethyl)-1,2,4-oxadiazol-5-yl]phenyl]carbamate;
[1-[2-[(Methylsulphonyl)amino]ethyl]-4-piperidinyl]methyl[2-[3-(phenylmethyl)-1,2,4-oxadiazol-5-yl]phenyl]carbamate;
1-[2-[(Methylsulphonyl)amino]ethyl]-4-piperidinyl]methyl[2-(3-methyl-1,2,4-oxadiazol-5-yl)phenyl]carbamate;
[1-[2-[(Methylsulphonyl)amino]ethyl]-4-piperidinyl]methyl][2-[3-(1,1-dimethylethyl)-1,2,4-oxadiazol-5-yl]phenyl]carbamate monohydrochloride;
[1-(1-Methylethyl)-4-piperidinyl]methyl[2-(3-methyl-1,2,4-oxadiazol-5-yl)phenyl]carbamate;
[1-(1-Methylethyl)-4-piperidinyl]methyl[2-(3-methyl-1,2,4-oxadiazol-5-yl)phenyl]carbamate;
N-[2-[4-[[[[2-(5-Methyl-1,2,4-oxadiazol-3-yl)phenyl]amino]carbonyl]amino]methyl]-1-piperidinyl]ethyl]methanesulphonamide;
[1-[2-[(Methysulphonyl)methyamino]ethyl]-4-piperidinyl]methyl[2-(3-methyl-1,2,4-oxadiazol-5-yl)phenyl]carbamate;
1-(Phenylmethyl)-4-piperidinyl[2-(3-methyl-1,2,4-oxadiazol-5-yl)phenyl]carbamate;
[1-[(Phenylmethyl)-4-piperidinyl]methyl[2-(3-methyl-1,2,4-oxadiazol-5-yl)phenyl]carbamate;
and pharmaceutically acceptable salts thereof.
8. [1-[2-[(Methylsulphonyl)amino]ethyl]-4-piperidinyl]methyl[2-(3-methyl-1,2,4-oxadiazol-5-yl)phenyl]carbamate; and pharmaceutically acceptable salts thereof.
9. The compound of claim 8 in the form of its butenedioate salt.
10. The compound of claim 8 in the form of its methanesulphonate salt.
11. A compound as claimed in claim 1 for use in therapy.
12. A pharmaceutical composition comprising a compound as claimed in claim 1 together with a pharmaceutically acceptable carrier.

* * * * *